(12) United States Patent
Nuttall et al.

(10) Patent No.: US 6,551,815 B1
(45) Date of Patent: Apr. 22, 2003

(54) IN SITU DENITRIFICATION

(75) Inventors: Herbert E. Nuttall, Albuquerque, NM (US); Yongming Lu, Savage, MD (US)

(73) Assignee: University of New Mexico, Albuquerque, NM (US)

( * ) Notice: Subject to any disclaimer, the term of this patent is extended or adjusted under 35 U.S.C. 154(b) by 0 days.

(21) Appl. No.: 09/423,411

(22) PCT Filed: May 8, 1998

(86) PCT No.: PCT/US98/09484

§ 371 (c)(1), (2), (4) Date: Feb. 4, 2000

(87) PCT Pub. No.: WO98/50177

PCT Pub. Date: Nov. 12, 1998

Related U.S. Application Data

(60) Provisional application No. 60/046,042, filed on May 9, 1997.

(51) Int. Cl.[7] .................................................. C12S 13/00

(52) U.S. Cl. .................... 435/262.5; 435/262; 210/610; 210/747

(58) Field of Search ......................... 435/262, 262.5, 435/179, 264; 423/DIG. 17; 588/249; 71/8–11, 64.11; 210/610, 611, 747; 252/184; 424/468–470; 502/404, 518; 504/117

(56) References Cited

U.S. PATENT DOCUMENTS

| | | |
|---|---|---|
| 3,829,377 A | 8/1974 | Hashimoato |
| 4,039,438 A | 8/1977 | Anderson |
| 4,683,064 A | 7/1987 | Hallberg et al. |
| 4,749,491 A | 6/1988 | Lawes |
| 4,970,000 A | 11/1990 | Eppler |
| 5,073,256 A | 12/1991 | Sieksmeyer et al. |
| 5,080,782 A | 1/1992 | Caplan et al. |
| 5,221,159 A | 6/1993 | Billings et al. |
| 5,316,832 A | 5/1994 | Groten et al. |
| 5,318,699 A | 6/1994 | Robertson et al. |
| 5,346,620 A | 9/1994 | Hendrix et al. |
| 5,348,653 A | 9/1994 | Rovel |
| 5,384,048 A | 1/1995 | Hazen et al. |
| 5,478,473 A | 12/1995 | Oshima |
| 5,490,934 A | 2/1996 | Schmid |
| 5,518,618 A | 5/1996 | Mulder et al. |

OTHER PUBLICATIONS

Nuttall, et al., "Preliminary Screening Results for In Situ Bioremediation at an UMTRA Site," 10 pages (May 10, 1996).

Nuttall, et al., "Preliminary Screening Results for In Situ Bioremediation at an UMTRA Site," *Waste Management 1996 Proceedings, Session 45* paper 6 (3 pages) (Feb. 10, 1996).

(List continued on next page.)

*Primary Examiner*—David A. Redding
(74) *Attorney, Agent, or Firm*—Jeffrey D. Myers

(57) ABSTRACT

A method of in situ biodenitrification of a contaminated site comprising providing to a contaminated site a phosphorous source, namely a polyphosphate or a trimetaphosphate. The phosphorous source is provided to a saturated zone or an unsaturated zone and a carbon source is also provided, most preferably acetate. The invention is also of an in situ biodenitrification apparatus (FIG. 3) comprising at least one extraction well for extracting subsurface water from a contaminated site, a container for mixing nutrients into the extracted water, and an injection well for re-introducing the extracted water to the subsurface. Preferably, at least three extraction wells are placed approximately on a circle having the injection well as a center, and a phosphorous source is introduced to the container, preferably a polyphosphate or a trimetaphosphate.

9 Claims, 12 Drawing Sheets

OTHER PUBLICATIONS

Nuttall, et al., "In Situ Bioremediation of Contaminated Groundwater at an UMTRA Site," *In Situ and On–Site Bioremediation: vol. 1*, Fourth International In Situ and On–Site Bioremediation Symposium, New Orleans, LA, pp 435–440, May 1, 1997.

Egli, T., et al., "Phosphate and Nitrate Removal," *Curr. Opin. Biotechnol.*, vol. 5, No. 3, pp 275–284 (1994) ABSTRACT only.

Lu, Yongming, "Sequential Bioremediation of Nitrate and Uranium in Contaminated Groundwater," *Dissertation, University of New Mexico*, pp. 1–261, Publication May 9, 1998.

SCHEMATIC DIAGRAM ILLUSTRATING THE SUBSTRATE/NUTRIENT
DELIVERY SYSTEM IN THE UNSATURATED ZONE

IN SITU DENITRIFICATION

CROSS-REFERENCE TO RELATED APPLICATIONS; GOVERNMENT RIGHTS

This application claims the benefit of the filing of U.S. Provisional Patent Application Ser. No. 60/046,042, entitled In Situ Biodenitrification Process, filed on May 9, 1997, and the specification thereof is incorporated herein by reference. The Government has rights to this invention pursuant to Contract No. PRO4-94AL638055.057 awarded by the U.S. Dept. of Energy.

BACKGROUND OF THE INVENTION

1. Field of the Invention (Technical Field)

The present invention relates to methods and apparatuses for in situ denitrification, most particularly biodentrification.

2. Background Art

Bioremediation is the use of microorganisms to convert harmful chemical compounds to less harmful chemical compounds in order to effect remediation of a contaminated site. The microorganisms are generally bacteria but can be fungi. The contaminants can be organics such as petroleum hydrocarbons and domestic wastewater or inorganics such as nitrate and metal ions. Microbial growth and metabolism require suitable nutrients to construct new cells and materials to supply energy through oxidation-reduction reactions.

The nutrients that are used to construct new cell components include inorganic or organic compounds that provide the major elements (carbon, oxygen, hydrogen, nitrogen, sulfur, phosphorus, etc.) to the cell. Elements that are not major components of building block material but are still necessary for growth (micro-nutrients) include such elements as Mg, Ca, K, Fe, Mn, Na, Zn, and Cl. Groundwater contaminated with nitrate and sulfate requires addition of only phosphorus nutrient and hydrocarbon substrate for the supply of major elements. While a variety of minerals are required by microorganisms, they are needed in trace amounts, and adequate amounts are normally present in most groundwater.

Microbial growth and metabolism need an energy supply. Microorganisms obtain their energy for metabolism and biosynthesis either by converting sunlight into chemical energy (phototrophs) or extracting energy from organic or inorganic chemicals (chemotrophs). Oxidation-reduction reactions are the basis of all energy-producing reactions, and adenosine triphosphate (ATP) is the principle energy-transport molecule of the cell. Microorganisms then use this energy to perform specific functions, one of which is biosynthesis of new cell components. Energy can be extracted from substrates in one of three ways: respiration, fermentation, and anaerobic respiration. Aerobic bacteria use oxygen as a terminal electron acceptor and oxidize carbon substrate to $CO_2$ (i.e., respiration). Some anaerobic bacteria use inorganic molecules such as $NO_3^-$, $NO_2^-$, or $SO_4^{2-}$ as electron acceptors with $CO_2$ as the final carbon oxidation product (i.e., anaerobic respiration), while others use organic molecules such as pyruvate as an electron acceptor with fermentation products such as lactic acid as a final carbon oxidation product (i.e., fermentation). Facultative bacteria have the capability of growing in the presence or absence of oxygen.

Denitrifying bacteria, which are able to use nitrogen oxides as electron acceptors in place of oxygen, are essentially facultative bacteria. Obligate anaerobes, such as sulfate reducing bacteria often survive in the presence of facultative bacteria. There are two nutritional types of microorganisms—those that obtain their carbon for biosynthetic processes from organic compounds (i.e., heterotrophs) and those that obtain their carbon for biosynthetic processes from $CO_2$ (i.e., autotrophs). Most denitrifying bacteria and sulfate reducing bacteria are heterotrophic and few can grow autotrophically.

Nitrate pollution in groundwater is a common problem in all European and North American countries. Nitrate contamination often exceeds the maximum contaminant limit of 10 mg N/L, and poses a major threat to drinking water supplies. The standard was imposed because nitrate is linked to infant methemoglobinemia ("blue baby" syndrome). The formation of nitroso-compounds which are known carcinogens also has been linked to nitrate. Conventional nitrate treatment technologies include reverse osmosis and ion exchange. Activated carbon adsorption in conjunction with pH adjustment has also been used in experimental studies to successfully remove nitrate. Biological denitrification is a technology mainly studied for surface water treatment. Compared to conventional technologies, biological denitrification is very cost-effective and is promising for in situ remediation, particularly as practiced with the present invention.

The main biological processes involving inorganic nitrogen are shown in FIG. 1. Nitrogen fixation involves the synthesis of cellular nitrogen compounds from elementary nitrogen. It is associated primarily with certain agricultural plants in which bacteria in a symbiotic or free living state. Deamination reactions are associated with the lysis of dying cells and the formation of ammonia from organic nitrogen compounds. Nitrification is the oxidation of $NH_4^+$ to nitrate, via nitrite, and is carried by nitrifying bacteria. With regard to nitrate metabolism, assimilation is defined as the conversion of nitrate to cellular organic nitrogen via ammonia, and dissimilation (or nitrate respiration) is defined as the oxidation of carbon compounds at the expense of nitrate which acts as the alternative electron acceptor to oxygen.

Denitrification is a special case of dissimilation in which gaseous nitrogens are end products. The principal products are nitrogen gas ($N_2$) and nitrous oxide ($N_2O$), though nitric oxide (NO) has occasionally been detected. During the denitrification process, nitrogen oxides serve as terminal electron acceptors instead of oxygen and are reduced by a unique suite of complex enzymes that conserve energy in several reductive steps by electron transport phosphorylation. The pathway of denitrification is thought to be:

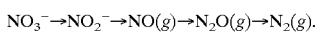

$$NO_3^- \rightarrow NO_2^- \rightarrow NO(g) \rightarrow N_2O(g) \rightarrow N_2(g).$$

The reduction of nitrate to nitrite is known as denitratation, and the reduction of nitrite is called denitritation. Each reaction step involves a different enzyme. For example, nitrate reductase (NaR) catalyzes the reduction of nitrate to nitrite and nitrite reductase (NiR) catalyzes the reduction of nitrite to gaseous products.

Nitrite and $N_2O$ are often observed to accumulate temporarily during denitrification. This accumulation can often been explained by relative differences in reaction rates for the different steps in the sequence. For example, when denitritation rate is higher than denitratation rate, nitrite is reduced as soon as it appears and so, it does not accumulate in the system. But if denitratation is faster than denitritation, nitrite build-up will be noticed. Several reasons have been suggested to explain this phenomenon: evolution of the microbial population, enzymatic adaptation to changes in the environment (particularly, dissolved oxygen concentration and pH), inhibition of nitrite reductase, or effect of external carbon loading.

Denitrifying bacteria, which are able to use nitrogen oxides as electron acceptors in place of oxygen with the evolution of gaseous products, are biochemically and taxonomically very diverse. Most bacteria are heterotrophs and some utilize one-carbon compounds, whereas others grow autotrophically on $H_2$ and $CO_2$ or reduced sulfur compounds. One group is photosynthetic. Most have all of the reductases necessary to reduce $NO_3^-$ to $N_2$, some lack $NO_3^-$ reductase and are termed $NO_2^-$ dependent, and others lack $N_2O$ reductase and thus yield $N_2O$ as the terminal product. Still other organisms possess $N_2O$ reductase but cannot produce $N_2O$ from $NO_3^-$ or $NO_2^-$. Among the denitrifying bacteria, the genus Pseudomonas, which includes the most commonly isolated denitrifying bacteria from both soils and aquatic sediments, may represent the most active denitrifying bacteria in natural environments. Some of them are $NO_2^-$ dependent, and some strains produce $N_2O$. Denitrifying pseudomonads include *P. denitrificans, P. fluorescens, P. stutzeri, P. aerogenes, P. aureofaciens, P. caryophylli,* and *P. chlororaphis.*

Increasing the population of denitrifying bacteria is the ultimate goal of denitrification. Natural in situ biological denitrification, which is too slow to do efficient groundwater remediation, can be promoted by adding suitable nutrients. Addition of a carbon substrate is required to increase the amount of denitrifying bacteria and, consequently, achieve a satisfactory degree of denitrification for groundwater with a low BOD (Biochemical Oxygen Demand) to nitrogen ratio. Amendment of sulfur and nitrogen is usually not necessary, because they are already typically present in the groundwater (in the form of sulfate and nitrate). Although ammonia ($NH_3$) is the most efficiently used nitrogen source for microbial synthesis since it can be incorporated directly into carbon skeletons to produce amino acids, nitrate and/or nitrite can be assimilated by many denitrifying bacteria to $NH_3$ with electrons supplied by $NADPH_2$ (reduced nicotinamide adenine dinucleotide phosphate). With regard to micro-nutrients, their addition is typically not necessary for in situ bioremediation, and may even have a negative impact on biological activity in soil. But the amendment of phosphorus nutrient is often essential for activating bacterial growth in the groundwater, and is best supplied as in the present invention.

Many organic compounds including carbohydrates, alcohols, organic acids and amino acids can serve as effective carbon sources for heterotrophic denitrifying organisms. Methanol and ethanol are the most commonly used external carbon sources. Besides methanol and ethanol, other carbon sources have been used as electron donors for denitrification, including glucose, sucrose, isopropanol (in practice, isopropanol itself contributes little to denitrification while the converted acetone plays the main role of electron donor), ascorbic acid, lactic acid, acetate, and even hydrogen gas generated through the electrolysis of water. Acetate, lactate, glucose, methanol and ethanol are often employed for denitrification because these chemicals are relatively cheap and commercially available.

Phosphorus is an essential element for bacterial growth. Phosphorus appears in organic molecules primarily as a component of nucleotides such as ATP, which is important as a carrier of energy and phosphate, and as a constituent of nucleic acids. Typical phosphate concentrations in soil ranges from 50 to 5000 mg/L and in groundwater from 100 to 1000 µg/L, which can support fairly high cell density for in situ bioremediation. However, often a phosphorus nutrient has to be added. Consequently, phosphorus amendment for in situ denitrification is crucial to success of many denitrification sites.

To reiterate, bioremediation is driven by increasing the size and mass of microbial populations. Microorganisms must transform environmentally available nutrients to forms what are useful for incorporation into cells and synthesis of cell polymers. Reducing nutrients and synthesizing new cell mass requires energy. This energy is supplied through electron transfer from electron donors to terminal electron acceptors. The terminal electron acceptor used during metabolism is important for establishing the redox conditions and the chemical speciation in the vicinity of the cell. Common terminal electron acceptors include oxygen under aerobic conditions, and nitrate, Mn(IV), Fe(III), sulfate, and carbon dioxide under anaerobic conditions. Although uranium is toxic to microorganisms, reduction of U(VI) is also able to serve as terminal electron acceptor for some bacteria.

Contaminants in groundwater can include nitrate, U(VI), and sulfate. These inorganic chemicals can serve as electron acceptors for bacterial growth in anaerobic conditions. Consequently, the addition of electron donors is required for remediation purposes. Glucose acetate, ethanol, methanol and lactate are possible electron donors. Phosphorus is an essential element for bacterial growth. The amendment of phosphate needs to be employed to achieve appreciable remediation rates.

Microorganisms preferentially utilize electron acceptors that provide the maximum free energy during respiration. Of the common electron acceptors used by microorganisms, oxygen has the highest redox potential and provides the most free energy to microorganisms during electron transfer. The redox potentials of nitrate, U(VI), Fe(III), and sulfate are lower compared to the redox potentials of oxygen. Consequently, they yield less energy during substrate oxidation and electron transfer according to the order as shown in FIG. 2. The calculation of the redox potential data is summarized in Appendix 1 of Lu, "Sequential Bioremediation of Nitrate and Uranium in Contaminated Groundwater", unpublished Ph.D. Dissertation, University of New Mexico (publication anticipated after May 9, 1998), and the entirety of the dissertation is incorporated herein by reference. When amended with carbon substrates (electron donors), the indigenous bacteria (likely a consortium of bacteria with many different species) in the groundwater will consume dissolved oxygen first and then nitrate. Only after all nitrate is consumed, will anaerobic bacteria then begin to grow and use ferric ion (by IRB) or sulfate (by SRB) as alternate electron acceptors. The stepwise reactions are also shown in FIG. 2.

If groundwater is amended with potassium acetate as an carbon substrate (electron donor) along with a phosphorus nutrient, and assuming that acetate can support the growth of denitrifying bacteria, IRB (ion-reducing bacteria) and SRB (sulfate-reducing bacteria), and is oxidized to carbon dioxide, the total reactions being shown in Equations 1–6:

$$CH_3COO^- + 2O_2 \rightarrow 2HCO_3^- + H^+ \qquad (1)$$

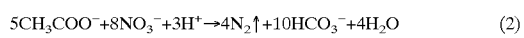

$$5CH_3COO^- + 8NO_3^- + 3H^+ \rightarrow 4N_2\uparrow + 10HCO_3^- + 4H_2O \qquad (2)$$

Denitrifying bacteria are facultative, so they can use both dissolved oxygen and nitrate as electron acceptors. Denitrifying bacteria will consume oxygen first and then nitrate. As will be shown in the experimental parts of the dissertation, consumption of oxygen is the prerequisite of denitrification. The redox potential (Eh) value decreases continuously during denitrification, and is lower than −100 mV after the completion of denitrification. Neutral pH and low Eh are two essential growth conditions of IRB and SRB. The stepwise reactions in anaerobic conditions are:

$$CH_3COO^- + 4UO_2(CO_3)_2^{2-} + 4H_2O \rightarrow 4UO_2 + 10HCO_3^- + H^+ \quad (3)$$

$$CH_3COO^- + 8Fe(OH)_3 + 6HCO_3^- + 7H^+ \rightarrow 8FeCO_3 + 20H_2O \quad (4)$$

$$CH_3COO^- + SO_4^{2-} \rightarrow HS^- + 2HCO_3^- \quad (5)$$

$$CH_3COO^- + 8FeOOH + 6HCO_3^- + 7H^+ \rightarrow 8FeCO_3 + 12H_2O \quad (6)$$

The present invention is of novel methods and apparatuses for drastically improving the rate and efficiency of in situ denitrification, as discussed in the following sections.

SUMMARY OF THE INVENTION (DISCLOSURE OF THE INVENTION)

The present invention is of a method of in situ biodenitrification of a contaminated site comprising providing to a contaminated site a phosphorus source, namely a polyphosphateor a trimetaphosphate. In the preferred embodiment, the phosphorus source is provided to a saturated zone or an unsaturated zone and a carbon source is also provided, most preferably acetate.

The invention is also of an in situ biodentrification apparatus comprising at least one extraction well for extracting subsurface water from a contaminated site, a container for mixing nutrients into the extracted water, and an injection well for re-introducing the extracted water to the subsurface. In the preferred embodiment, at least three extraction wells are placed approximately on a circle having the injection well as a center, and a phorphorus source is introduced to the container, preferably a polyphosphate or a trimetaphosphate.

The invention is further of a method of biodentrification of a contaminated site comprising: sampling groundwater of the contaminated site; determining levels of nitrate contamination and potential nitrate consuming bacteria from the sampled groundwater; choosing preferred nutrients to be injected into the contaminated site; configuring size, geometry, and pumping rates for wells to be installed at the site; and installing and operating one or more well clusters at the site until the subsurface is denitrified to a desired level. In the preferred embodiment, one or more of the following steps are additionally employed: determining levels of nutrients, determining levels of dissolved oxygen, determining levels of phosphates, generating reaction curves for predetermined constituents at the site, verifying shape of the reaction curves to determine whether significant chemical reactions other than denitrification are occurring, gathering contaminate concentration and hydrological data at the site, and installing and testing a single well cluster at the site.

A primary object of the present invention is to provide biodenitrification methods and apparatuses for drastically improving the rate and efficiency of the process in contaminated sites.

A primary advantage of the present invention is reduction of plugging of infiltration wells by the use of polyphosphate or trimetaphosphate, preferably trimetaphosphate, as the forms of phosphate for injection.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

BEST MODES FOR CARRYING OUT THE INVENTION

The present invention is of methods and apparatuses for in situ biodenitrification of groundwater and soil. The contaminate nitrates are converted to harmless nitrogen gas through the bacterial metabolism process via the following reaction:

nutrient+bacteria+nitrate→nitrogen gas+water+carbon dioxide $$NO_3^- \rightarrow NO_2^- \rightarrow O\ N_2\uparrow \quad (7)$$

Using acetate as the preferred organic nutrient, the overall reaction is:

$$5CH_3COO^- + 8NO_3^- + 3H^+ \rightarrow 4N_2\uparrow + 10HCO_3^- + 4H_2O \qquad (8)$$

In practice, there are two rate limiting reactions, name the conversion of nitrate to nitrite, $$CH_3COO^- + 4NO_3^- \rightarrow 4NO_2^- + 2HCO_3^- + H^+, \qquad (9)$$

and subsequently the conversion of nitrite to nitrogen gas, $$3CH_3COO^- + 8NO_2^- + 5H^+ \rightarrow 4N_2\uparrow + 6HCO_3^- + 4H_2O. \qquad (10)$$

Figure 3:
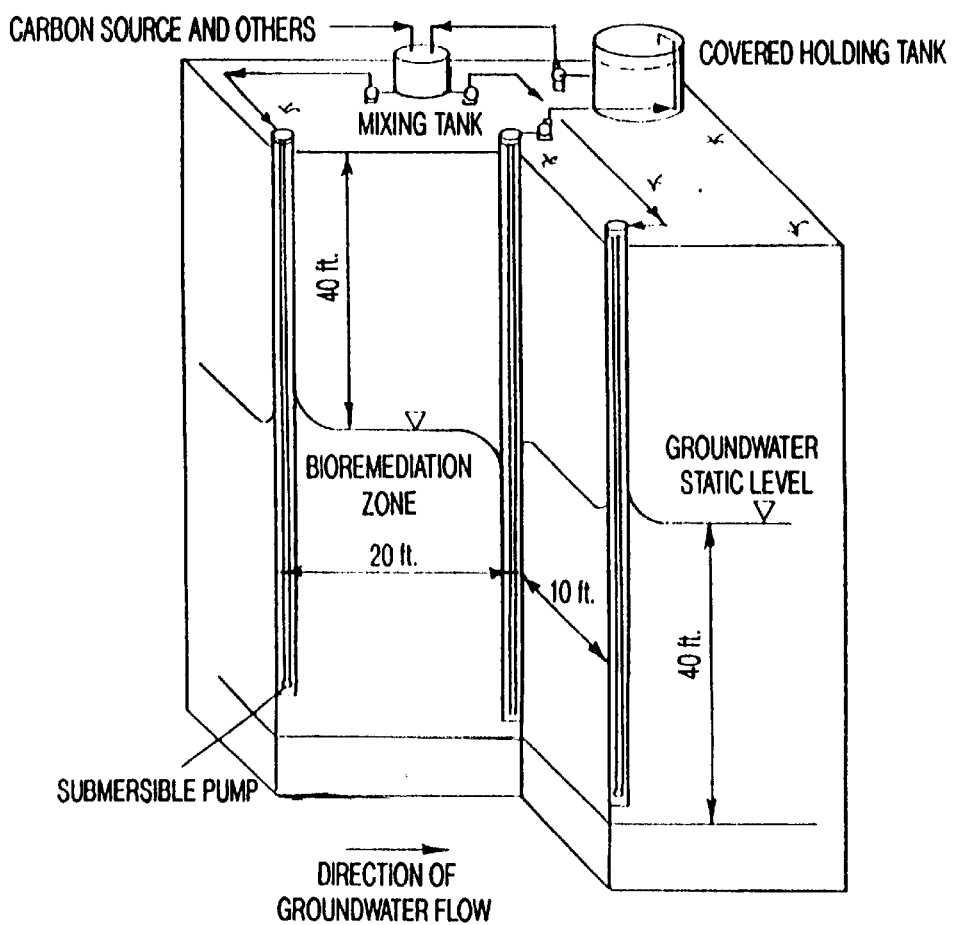
FIG. 3 is a schematic diagram of a well configuration employable with the present invention.
Figure 3A:
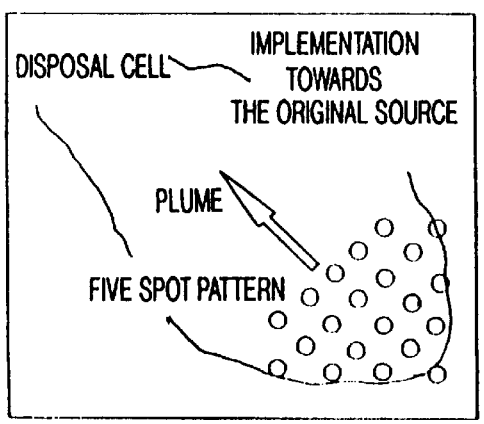
Figure 3B:
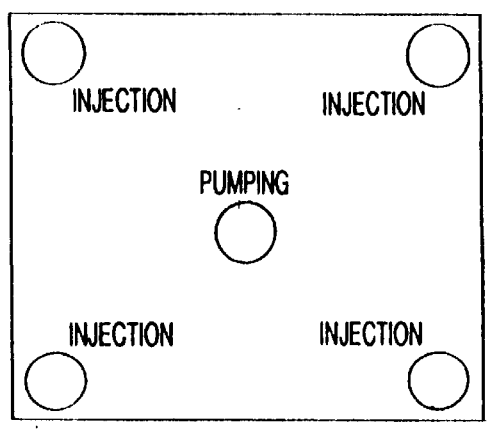

The in situ process can be established in many geometries. The simplest is a single borehole injection of nutrients and denitrifying bacteria (if necessary). A series of extraction and injection wells pattern are preferably employed. FIG. 3 illustrates this concept in the saturated zone using at least two extraction and one injection well, and preferably four extraction wells placed on a circle having the injection well as a center. The invention can also be applied to the unsaturated zone (UZ) in which boreholes provide access but excess water is required to saturate the formation. The invention may be employed in either the saturated or unsaturated zone.

At most potential remediation sites, the indigenous bacteria are lacking an appropriate and/or adequate carbon energy source (substrate) and they may be lacking phosphate (nutrient). These two water-soluble substances must, in general, be provided to the indigenous bacteria. A number of carbon sources that can greatly accelerate the process include acetate, methanol, ethanol, glucose, lactate, and other short chain hydrocarbons.

Figure 10:
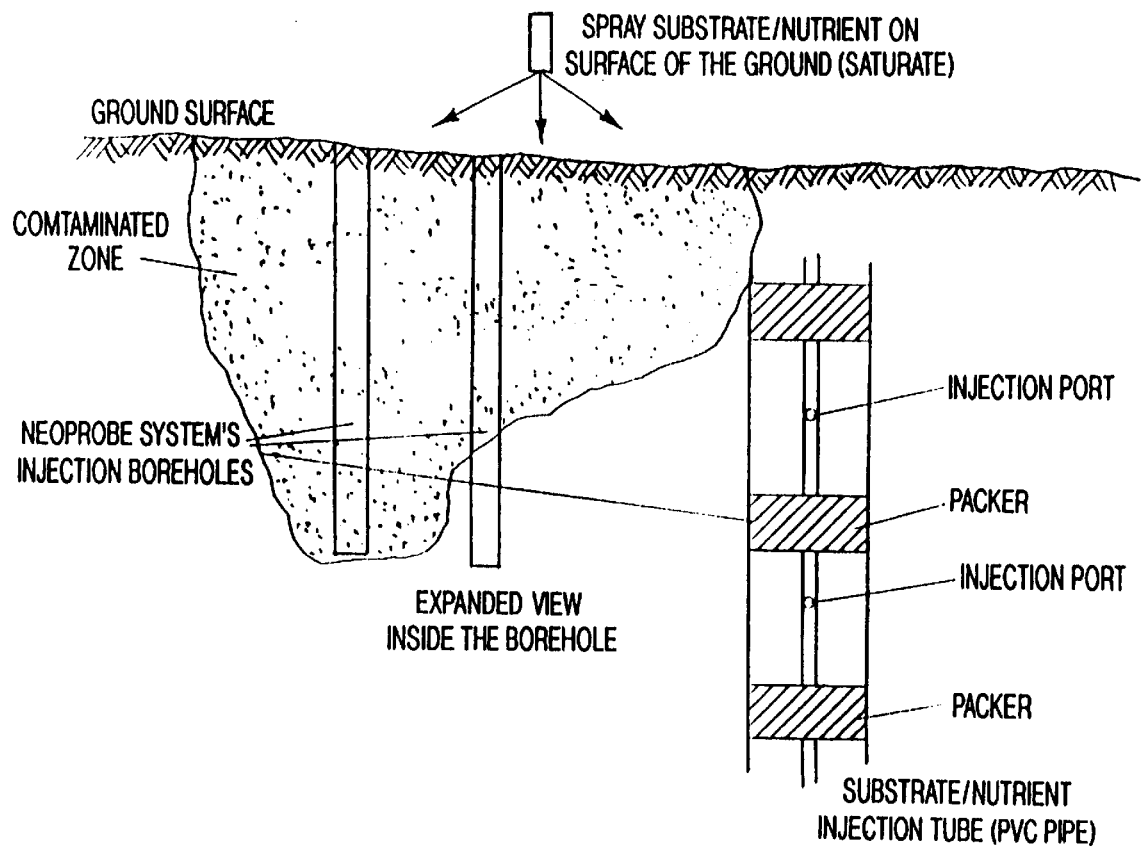
FIG. 10 is a schematic diagram illustrating the substrate/nutrient delivery system of the invention in the unsaturated zone.

When one applies the optimal substrate/nutrients, the in situ system is mixing or mass transfer limited. This means that to optimize the process one must focus on the design of the delivery system. In the UZ, the problem is distributing substrate/nutrients throughout the contaminated soil. To do this, as shown in FIG. 10, one needs numerous inexpensive wells and solution added to the soil surface. The inexpensive wells are preferably made using PVC pipe with inflatable packers and one injector between packers. The objective is to have about one injector per cubic meter of soil in the UZ. With this design, the soil can be quickly decontaminated. If there is excess substrate/nutrient which reaches the groundwater, this will be beneficial and initiate denitrification in the SZ.

Figure 11A:
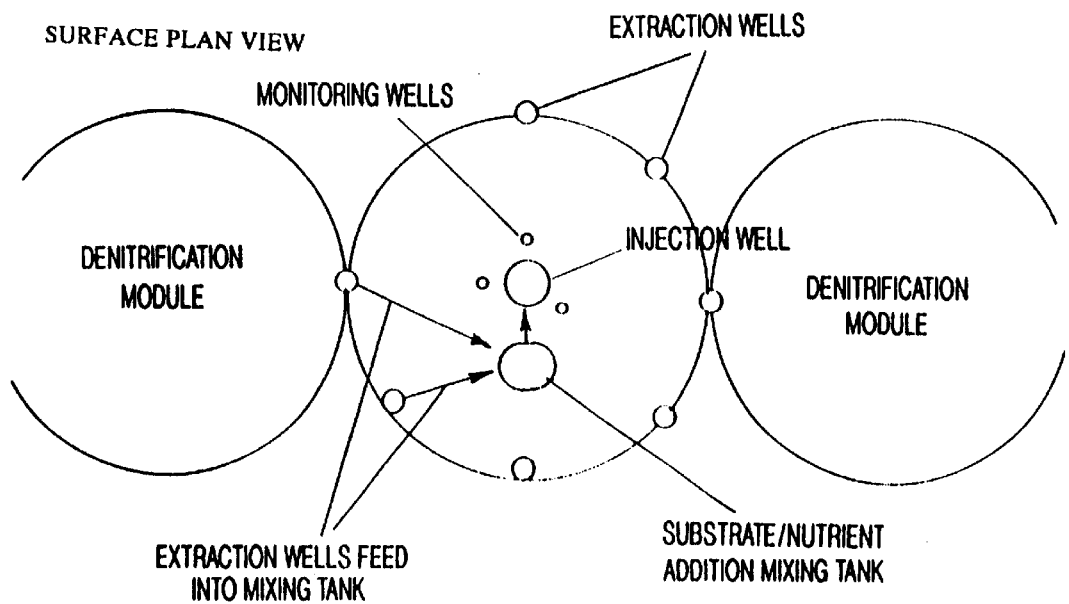
FIGS. 11a, 11b are a schematic diagram illustrating the "Wagon Wheel" substrate/nutrient delivery system of the invention in the saturated zone.
Figure 11B:
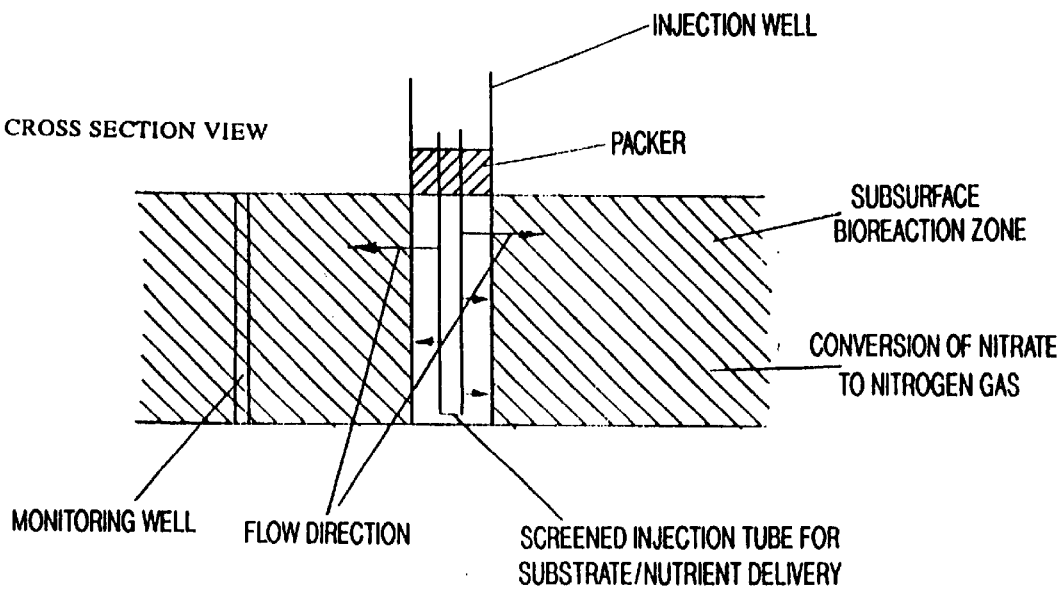

There are several useful designs for an SZ delivery system. The preferred design is a "wagon wheel" approach, as shown in FIG. 11, with one injection well equipped with a packer and a "wagon wheel" of extraction wells surrounding this one injection well. Nitrate contaminated groundwater is pumped from the extraction wells, mixed with a predetermined amount of substrate/nutrients, and reinjected via the single injection well. The saturated zone surrounding the single injection well becomes a highly effective fixed bed biodenitrification reactor. The single injection well should have one or more monitoring wells located in the reactive zone. A key to successful operation is to avoid formation plugging by the biomass and assure complete denitrification. The diameter of the size of the "wagon wheel" is important as well as knowing the concentration of nitrate in the contaminated groundwater and the proper sequence of operation of the injection well. The injection is preferably pulsed with and without substrate/nutrient addition to avoid plugging or pressure loss in the injection bore hole. For each module in a plume, the decontamination strategy can be customized in size and operation to match variations in plume hydrology, and contamination levels. For a typical site, a single module with a diameter of 100 meters may operate for about 6 months in order to fully remediate the zone affected by the foot print of the model on the plume. For a large plume, several module may be needed. Modules may be clustered to achieved plume containment where appropriate.

The present invention relies on the presence of denitrifying bacteria within the mixed bacteria population in the subsurface. Denitrifying bacteria are ubiquitous in the subsurface environment and only in sterile areas would one not be able to cultivate in situ a large population of denitrifying bacteria. Hence there is typically no requirement to amend with ex situ bacteria. Though the species of denitrifying bacteria will likely be different at each site, the denitrification functionality will be approximately the same. Given more time this section could contain much of our detailed denitrification results. A typical denitrification results graph is given in FIG. 6, which illustrates that denitrification follows the laws of thermodynamics in that the various reactions follow the oxidation-reduction potential. Note that the first reaction is the conversion of dissolved oxygen followed by denitrification. With this knowledge one is able to closely control the denitrification reaction in either the laboratory or the field.

Phosphorus is an essential element for bacterial growth. Phosphorus appears in organic molecules primarily as a component of nucleotides such as ATP, which is important as a carrier of energy and phosphate, and as a component of nucleic acids. Amendment of phosphate is critical for successful groundwater denitrification where there are little phosphorus compounds in groundwater or soil.

Nearly all in situ bioremediation projects use orthophosphates as an added phosphorus source, but the addition of orthophosphates often leads to precipitation of insoluble phosphates, which plug infiltration wells and surrounding aquifers, and hence short migration of phosphorus source. In addition to phosphate precipitation, sorption of orthophosphate to soil is very strong. No mobilization or solubilization of these retarded orthophosphates is observed in normal groundwater with a pH of 6 to 9. It is often difficult to control the phosphate precipitation with $Ca^{2+}$ and $Mg^{2+}$ (mainly calcium phosphates) during in situ denitrification.

Concerning the precipitation of orthophosphate and its sorption to soil, and hence short migration of phosphorus source, different organic and inorganic phosphates were considered for use in the present invention. Two inorganic phosphates were discovered which had unexpected advantages. The first source is polyphosphate, $(NaPO_3)_n$, with a different chain length from diphosphate $(Na_4P_2O_7)$, tripolyphosphate $(Na_5P_3O_{10})$, to $Na_{20}P_{18}O_{55}$. With increasing chain length (>5 P-atoms) of polyphosphates, the intensity of their interaction with soil decreases. The shorter polyphosphates such as diphosphate, tripolyphosphate also exhibit interaction with the soil matrices, but their retardation is more reversible than the retardation of orthophosphate. However, polyphosphates degrade rapidly in soil and form ortho-compounds. The other preferred source is trimetaphosphate (TMP), $Na_3P_3O_9$. TMP is a ring compound, and hence is more stable than polyphosphates. TMP has a slow rate of hydrolysis and its sorption in soils is also low.

Figure 4:
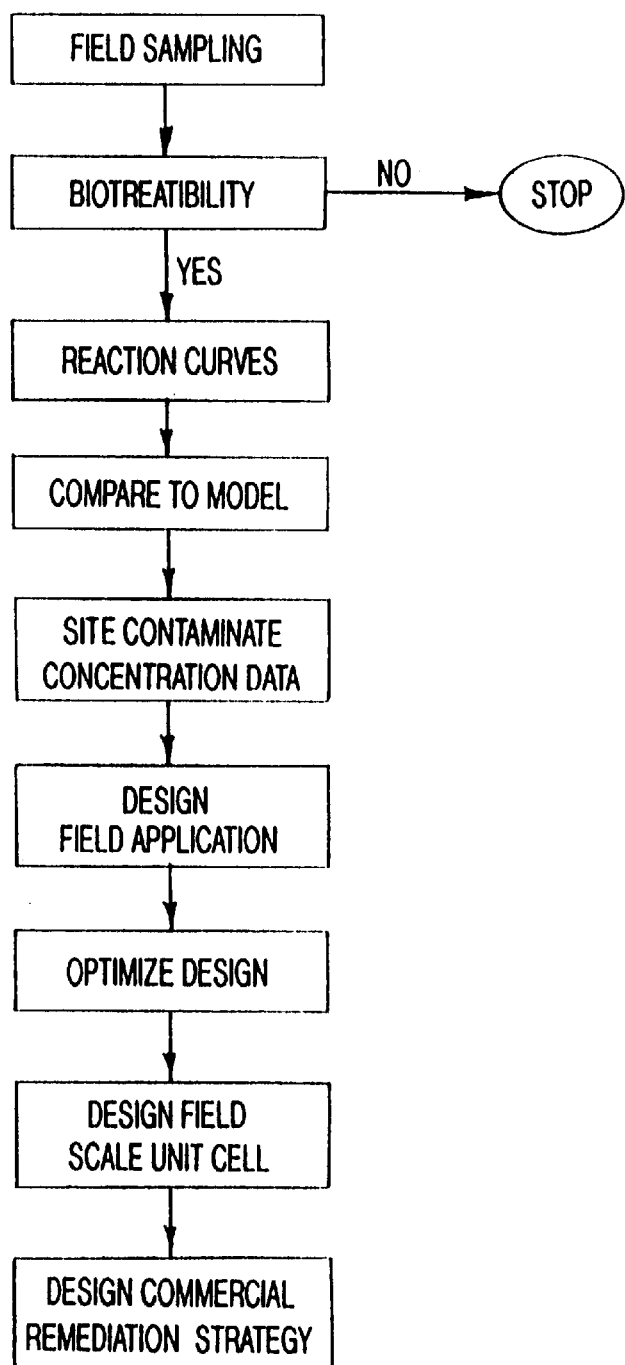
FIG. 4 is a flow chart of the preferred method of designing a field implementation to denitrify a contaminated site.

Referring to FIG. 4, in establishing an appropriate biodenitrification regime for a particular contaminated site, the following steps of the invention are preferably employed:

1. Field sampling of groundwater and if possible soil. The ground water and soil samples provide critical information about the level of nitrate contamination and if the media is lacking in nutrients such as phosphate. Also the level of dissolved oxygen (DO) is measured since DO is used first by the bacteria as an electron acceptor.

2. Laboratory screening for biotreatability and choice of amendments (carbon source) plus nutrient (phosphate). This determines whether samples from the site can be biotreated for nitrate and which substrate and nutrient is optimal for rate and minimum biomass production. This step also gives an indication of the initial concentrations of bacteria in the water and soil by the rate of the reaction.

3. Generation of type or reaction curves for key constituents (nitrate, nitrite, pH, DO, ORP, conductivity, amendment). Curves are generated using the selected substrate and nutrient. The shape of these rate curves should be reproduced in the field.

4. Verify shape and nature of reaction curves versus mathematical model. From mathematical models such as those in the unpublished Lu dissertation, one can determine if the measured rate curves are consistent and if denitrification is the only operating reaction.

5. Gather and review site contaminate concentration data (contours). This is the first step in the design of the field implementation of the denitrification process.

6. Gather and review site hydrological data. Hydrological data must be carefully considered in designing the commercial remediation scheme.

7. Design field application (configure the size, geometry and pumping rates for the amendment addition). Using information from the above steps, an appropriate field system is designed.

8. Optimize design to minimize costs and remediation time. The initial field design is optimized to minimize both costs and remediation time.

9. Design field scale unit cell. A single unit cell or pivotal injection module is designed and tested prior to full field implementation of the commercial concept.

10. Design and implement large scale plume remediation strategy. The appropriate system design is created and implemented in the field.

INDUSTRIAL APPLICABILITY

The invention is further illustrated by the following non-limiting examples.

EXAMPLE 1

Denitrification with Polyphosphate

Figure 8A:
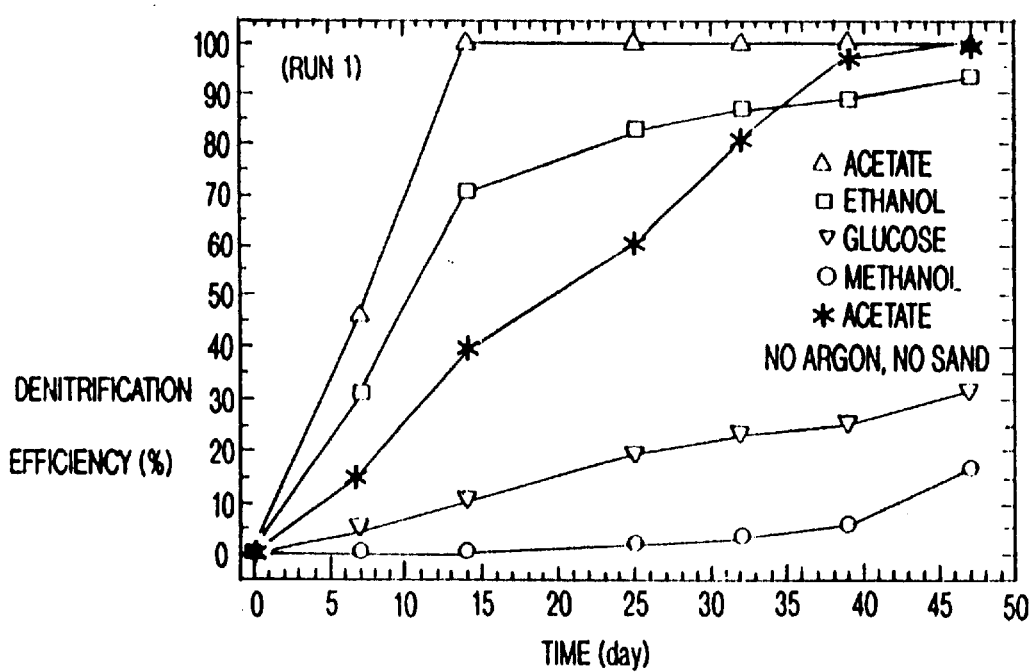
FIGS. 8(a) and (b) are graphs of denitrification efficiencies versus time for groundwater at 23±1° C., with each serum bottle containing approximately 100 mL groundwater, 8 g core sand, 100 g/L $NaPO_3$ (polyphosphate) and a carbon substrate (either acetate, ethanol, glucose or methanol), with purging by argon gas for 15 minutes.
Figure 8B:
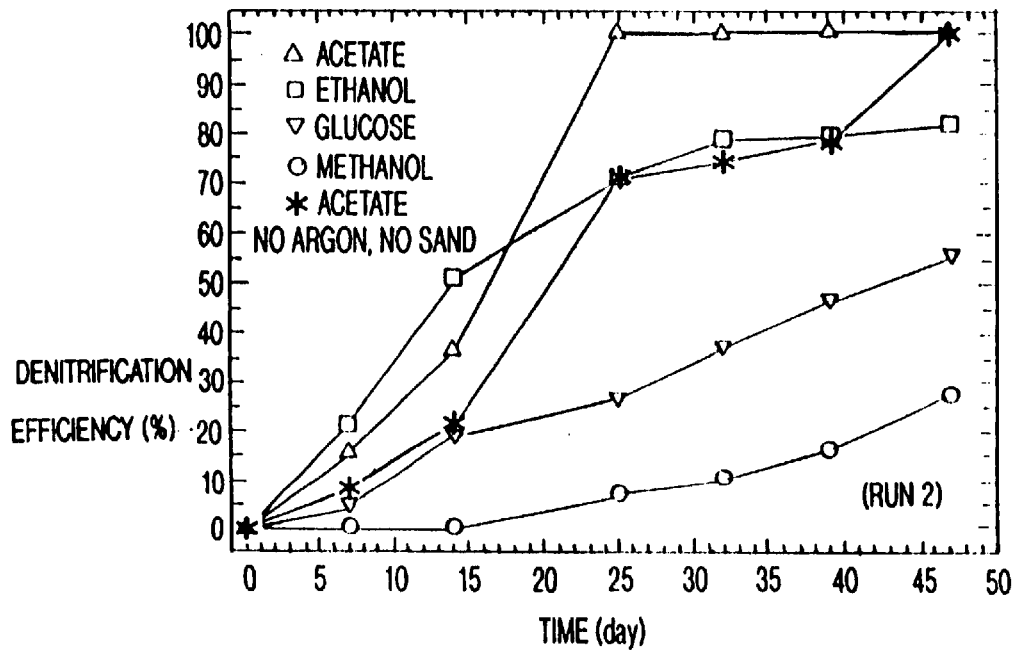

The denitrification profiles of groundwater amended with polyphosphate, $(NaPO_3)_n$ (typical value of n=17), and different carbon sources (acetate, ethanol, methanol and glucose) with the presence of core sand are shown in FIGS. 8(a) and (b). Experiments were run in serum bottles at room temperature (ca. 23±1° C.). The concentration of polyphosphate was 100 mg $NaPO_3$/L. The initial molar ratios of acetate to nitrate and glucose to nitrate were approximately 10:8 and 11:24 respectively (minimum C/N ratio for complete denitrification were 5.7:8 and 7:24 respectively as shown in Table 1), and hence no carbon limitation was present in these two experiments. The initial molar ratios of ethanol to nitrate and methanol to nitrate were about 5:12 and 5.5:6 respectively (minimum C/N ratio for complete denitrification were 6.5:12 and 6:6 respectively as shown in Table 1), and hence complete nitrate reduction could not be reached for these two experiments. Nitrite was an intermediate of denitrification process found in all of the experiments, and one mole of $NO_2^-$ was assumed to be equivalent to 0.6 mole of $NO_3^-$ when nitrate removal efficiency was calculated.

TABLE 3.3

Minimum Carbon/Nitrogen (C/N) ratios for nearly complete denitrification and theoretical yield coefficient (Y*) in base of nitrate (DW = dry weight).

| Carbon source | C/N molar ratio | Molar ratio of carbon source to nitrate | Y* (g DW cell/g $NO_3^-$) |
|---|---|---|---|
| Methanol | 1.000 | 6:6 | 0.079 |
| Ethanol | 1.083 | 6.5:12 | 0.118 |
| Acetate | 1.425 | 5.7:8 | 0.055 |
| Glucose | 1.750 | 7:24 | 0.158 |
| Lactate | 2.000 | 8:12 | 0.238 |

*Represents apparent yield for the whole denitrification process.

As shown in FIGS. 8(a) and (b), nitrate reduction with acetate as a carbon source was completed in 15 to 25 days. For ethanol, nitrate reduction stops after about 30 days (ethanol added was insufficient for complete denitrification). For these two carbons, the denitrification time with polyphosphate is about 5 to 10 days longer than that with orthophosphate. The reasons are likely that: (1) Microorganisms can only use orthophosphate for biochemical processes, hence the hydrolysis rate of polyphosphate to orthophosphate, if it is not fast enough, will control the denitrification rate; and (2) The hydrolysis rate of polyphosphate is mainly controlled by biological activity besides chemical effect at low temperature. The denitrification rate with glucose and methanol are much lower than that with acetate and ethanol, hence for glucose and methanol, the denitrification rate decreases due to the application of polyphosphate are much more significant compared to those amended with acetate and ethanol.

For all experiments amended with polyphosphate, white precipitates appeared while purging with argon. It was believed that hydrolysis of polyphosphate was accelerated by this purging process, and hydrolyzed species of polyphosphates precipitated with $Ca^{2+}$ and $Mg^{2+}$ (mainly $Ca^{2+}$) ions. In the absence of sandstone, very limited nitrate reduction (5% of nitrate was reduced when acetate was amended, and 0–2% of nitrate was reduced when ethanol, methanol or glucose was amended) was found after two months. This phenomenon verified the positive function of sand again for the groundwater denitrification if amended phosphates had precipitated (see Table 2).

TABLE 3.4

The mechanisms related to the pH change during denitrification process

Denitrification reactions which leads to pH change

| | | |
|---|---|---|
| Denitratation | $4\ NO_3^- + CH_3COO^- \rightarrow 4\ NO_2^- + 2\ HCO_3^- + H^+$ | (3.21) |

TABLE 3.4-continued

The mechanisms related to the pH change during denitrification process

| | | |
|---|---|---|
| Denitratation | $8\ NO_2^- + 3\ CH_3COO^- + 5H^+ \rightarrow 4\ N_2 \uparrow + 6\ HCO_3^- + 4\ H_2O$ | (3.22) |
| | Factors which buffer the pH | |
| Balance of carbonate species in solution and on the sand surface | $CO_2(g) \longleftrightarrow H_2CO_3^* \longleftrightarrow HCO_3^- \longleftrightarrow CO_3^{2-}$ | (3.19) |
| | $Me^{2+} + HCO_3^- + OH^- \longleftrightarrow MeCO_3(s) + H_2O$ | (3.20) |
| Balance of phosphate species in solution and on the sand surface | $H_3PO_4 \longleftrightarrow H_2PO_4^- \longleftrightarrow HPO_4^{2-} \longleftrightarrow PO_4^{3-}$ | (3.23) |
| | $Me^{2+} + HPO_4^{2-} \longleftrightarrow MeHPO_4(s)$ | (3.24) |
| Balance of acetate species | $CH_3COOH \longleftrightarrow H^+ + CH_3COO^-$ | |
| Ion exchange with sand | $Sand\text{-}Me + 2\ H^+ \longleftrightarrow Sand\text{-}2H + Me^{2+}$ | |

Me = Metal ion with valence of 2

Successful denitrification was found in the presence of high dissolved oxygen. The nitrate reduction for the experiment amended with acetate and polyphosphate in the absence of core sand and without purging with argon is shown in FIGS. 8(a) and (b) as well. White precipitates were not found until a week later. Nitrate reduction completes in 40 to 47 days. The denitrification rate is lower than that with core sand present. It is partly due to the presence of oxygen in the serum bottle. The water sample had dissolved oxygen around 4 mg/L, and was further oxygenated while transferring water from a 1 L plastic bottle to serum bottles. On the other hand, about 60 mL headspace of the serum bottle is air which contributes a major amount of oxygen in this sealed batch system. This result demonstrated that the indigenous denitrifying bacteria are facultative. Nitrate was used as an alternate electron acceptor after oxygen was depleted. The dissolved oxygen in the groundwater does not inhibit the activity of indigenous denitrifying bacteria. In Case 3 as shown in Table 2 (orthophosphate was used) in which both phosphate and trace minerals precipitated, the availability of both phosphorus and trace minerals in the soluble form for denitrifiers is the reason for the relatively faster denitrification rate even if large amount of oxygen was present. The phosphorus in solution is more bioavailable than that precipitated. As polyphosphate precipitate was not found until a week later, the plugging problem of the infiltration wells due to the precipitation of insoluble phosphate salts is solvable.

EXAMPLE 2

Denitrification with Trimetaphosphate

Figure 9A:
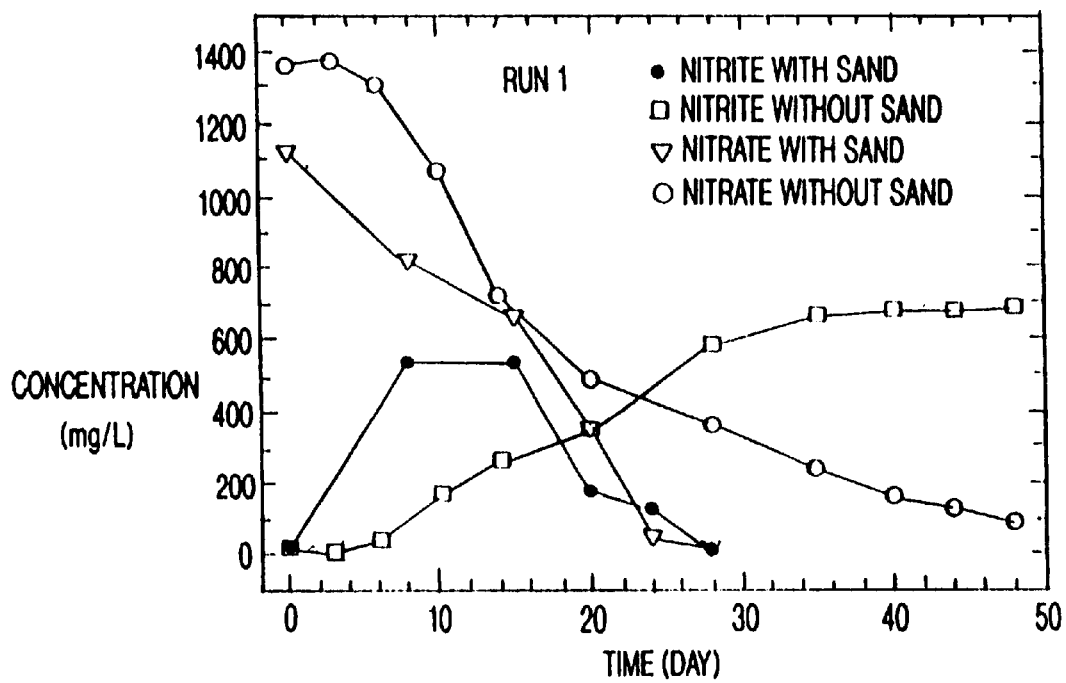
FIGS. 9(a) and (b) are graphs of concentrations of nitrate and nitrite versus time during denitrification of groundwater at 16° C., with each serum bottle containing approximately 100 mL goundwater 8 g core sand, 100 mg/L $NaPO_3$ (trimetaphosphate), and potassium acetate.
Figure 9B:
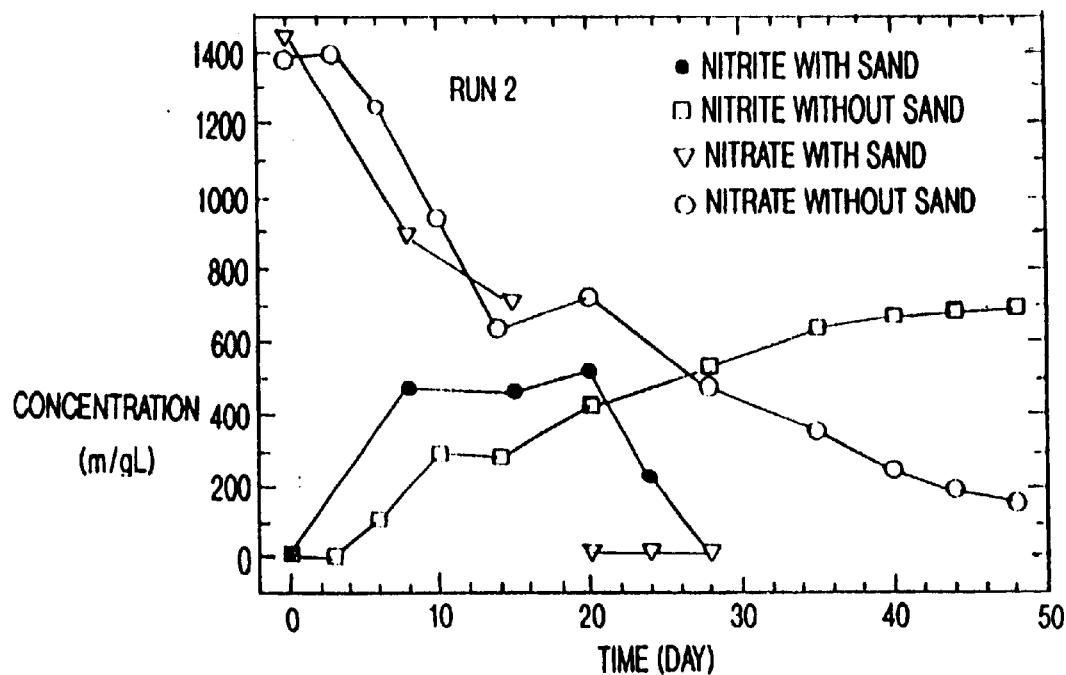

The denitrification profiles of groundwater amended with TMP and acetate with or without the presence of core sand are shown in FIGS. 9(a) and (b). Experiments were run in serum bottles at 16° C. The concentration of TMP was 100 mg NaPO₃/L. No phosphate precipitate was found while purging with argon, even in two weeks. This time is long enough for phosphate transportation into the whole contaminated aquifer, and no plugging problem of the infiltration wells due to the precipitation of insoluble phosphate salts will happen if the wells are designed properly. As shown in FIGS. 9(a) and (b), denitrification is complete in 28 days with the presence of sand. This is 11 days longer than that amended with orthophosphate. The hydrolysis rate of TMP limits the whole denitrification rate, although the nitrate reduction rate is also slow at 16° C. even amended with orthophosphate. However, this time difference will not be a critical issue for the in situ operation. A much quicker denitrification rate was also found with sand present compared to the experiments without the presence of sand. This phenomenon confirmed the positive effect of sand materials on in situ denitrification.

Comparing to the stepwise nitrate reduction phenomenon, i.e., nitrate is reduced to nitrite first and then nitrite begins to be reduced, simultaneous reduction of nitrate and nitrite is found for the experiments amended with TMP with sand in the system as shown in FIGS. 9(a) and (b). However, for the experiments without the presence of sand, similar stepwise nitrate reduction is found. This may be because of the difference between denitrifying bacteria stimulated or because of differences in metabolism mechanisms expressed even though the same type of denitrifiers were stimulated (simultaneous reduction of nitrate and nitrite was found for the experiments amended with ethanol and TMP as well (data not shown)).

The application of TMP as a phosphorus compound was not only applicable to the UMTRA site tested, above, but to other sites as well. In situ denitrification experiments with groundwater collected in the Mountainview area of New Mexico showed that denitrification via indigenous bacteria worked successfully after the groundwater was amended with potassium acetate and 20 mg TMP/L, but did not work without TMP. Denitrification worked successfully either in the presence or absence of sand, and either purged or without purged with argon (the serum bottle was collected full of water previously, and 20 mL water was sucked out, and therefore only dissolved oxygen was present), or even in the presence of about 20 mL air in a 160 mL serum bottle. The batch experiment has been scaled up to 1200 gallon successfully.

The column experiments for the groundwater denitrification at the Mountainview site demonstrated that the column was not plugged after ten batch runs for the system in which acetate and TMP was amended, but the column was plugged after three batch runs for the system in which ethanol and TMP was amended. This result is consistent with the finding of the unpublished Lu dissertation that the apparent yield coefficient for the system amended with ethanol is higher than that amended with acetate.

EXAMPLE 3

Tuba City, Ariz., UMPTRA Site

In situ biological denitrification was studied as a groundwater remediation process with nitrogen as the final product at an UMTRA site in Tuba City, Ariz. Nitrate contaminated groundwater and soil from the contaminated field site were used, and in all experiments the initial nitrate concentration was about 1300 mg/L and the pH was 7.5–8. Denitrification was studied in a 2.5 L fermentor and in 120 mL serum bottles using a water to soil ratio of 100 mL/8 g and indigenous denitrifying bacteria naturally present in the groundwater. Oxygen was removed initially by purging with argon for 15 minutes. Both carbon and phosphorus sources were found to be essential for promoting denitrification. Variables investigated include carbon (methanol, ethanol, glucose, acetate, and lactate) and phosphorous (orthophosphate, polyphosphate, trimetaphosphate) sources, C/N ratio, temperature (23±1° C. and 16° C.). Nitrate, nitrite, carbon source, and pH changes were monitored during denitrification. Eh was indicated using a resazurin dye. Denitrification was complete in all cases after 40 days at 23±1° C. The completion times varied from 14–40 days depending upon type of carbon source. The initial C/N molar ratios for complete denitrification (<1 mg/L for N) were 1.000, 1.083, 1.425, 1.750, or 2.000 using methanol, ethanol, acetate, glucose or lactate as a carbon source respectively. Nitrite was identified as an intermediate species in all experiments, and the data showed a slight nitrite inhibition effect. For each carbon source, the stoichiometric equation is present, and a theoretical yield coefficient was determined from each stoichiometric equation. The pH was found to vary cyclically from 7.3 to 8.4 in experiment with acetate as a carbon source, and this variation was explained in terms of the denitratation rate, denitritation rate and carbonate buffering effects. In addition to orthophosphate, polyphosphate and trimetaphosphate can also support bacterial growth. Both polyphosphate and trimetaphosphate showed reduced calcium phosphate precipitation as compared to orthophosphate.

Groundwater was sampled from the inactive uranium processing site at Tuba City, Ariz. The water samples were kept in 1000 mL plastic bottles and reserved in a refrigerator. Nitrate was reduced via the activity of the indigenous denitrifiers naturally present in the water samples after amended with suitable nutrients.

Chemicals used for carbon amendment included methanol $CH_3OH$, ethanol $C_2H_5OH$, Glucose $C_6H_{12}O_6$, potassium acetate $KCH_3COO$, and sodium lactate $NaCH_3CH(OH)COO$ which was prepared by neutralizing lactic acid syrup, 85% (w/w), using NaOH solution. Chemicals used for phosphorus amendment included orthophosphate $KH_2PO_4$, trimetaphosphate $Na_3P_3O_9$ (Sigma Co.) and polyphosphate $(NaPO_3)_n$ (Aldrich Co.). All chemicals were A.C.S. reagent grade. Crushed sands were prepared by pulverizing the core samples (about 47 to 100 feet depth) from the Tuba City site using a pestle and mortar. This Navajo sandstone is a fine to fine grained unit with median grain size diameter ($d_{50}$) about 0.11 mm. The sandstone was kept without contamination by organic chemicals.

Stock solution mixtures with neutral pH and total volume less than 15 mL for denitrification amendment, including carbon source and phosphorus sources, 0.05 mL of a 0.2% resazurin solution (redox potential indicator), and 8 g crushed sand for part experiments, were added into a 160 mL serum bottle, which was then autoclaved at 121° C. (250° F.) for 20 min. Groundwater sample was added under aseptic environment after the bottle cooled down, and the serum bottle was sealed with a butyl rubber stopper and crimped with an aluminum seal. Total volume of the liquid was about 100 to 120 mL. The solution was then purged with argon gas through a 22 gauge long needle for 15 min to ensure that an anaerobic environment was maintained, and another needle was used for gas exhaustion at the same time. The exhaustion needle was taken out before the spinal needle was done, and the serum bottle was pressurized under 7–10 psig. To keep the gas phase sterile, a gas filter with 0.2 $\mu m$ pore size was used. Serum bottles were kept either at room temperature about 23±1° C. and shaken 2 to 3 times every day or kept at 16° C. in a Lindberg/Blue M constant temperature refrigerated shaker waterbath model RSWB3222A (A General Signal Company, NC). No denitrifying bacteria were inoculated to water samples, and pH was not controlled for all of the experiments. Denitrification process via the activity of the indigenous denitrifiers present in the groundwater was monitored. Disposable syringes were used for sampling.

The denitrification process with indigenous denitrifiers present in groundwater was monitored in a 2.5 L cylindrical glass reactor (BioFlo 3000, New Brunswick Scientific, NJ) stirred at 200 rpm. The pH was not controlled during the experiment. The water bath temperature was kept at 16° C. using a recirculating chiller (Model 1170, VWR Scientific). Groundwater, about 2.25 L, was amended with a stock solution of $KCH_3COO$ and $KH_2PO_4$ with neutral pH. The denitrification process in the reactor, which contained $KCH_3COO$ 2.5 g/L, $KH_2PO_4$ 100 mg/L, 0.2%(w/v) resazurin solution 0.5 mL/L, and crushed sand 80 g/L, was monitored by periodically measuring concentration change of acetate, nitrate and nitrite. The pH change was also recorded. Prior to addition with groundwater, the reactor was sterilized and flushed with argon gas to ensure anoxic condition. The reactor was continuously purged with argon gas for about 20 min after inoculated with groundwater. The exhaustion exit was then closed, and the reactor was pressurized under argon at about 7–10 psig. A gas filter with 0.2 $\mu m$ pore size was used to keep the gas phase sterile.

Concentrations of acetate, lactate, nitrate, nitrite, sulfate were measured through ion chromatographic (IC) analysis of liquid samples. The IC unit, Dionex DX 500 chromatography system (Dionex Co., CA), consists of a GP 40-1 gradient pump, an ED 40-1 electrochemical detector, and a LC 10-2 chromatography organizer with an Ionpac AS 11 analytical column (4 mm) and an ASRS-1 (4 mm) anion self-regenerating suppresser as its main components. This Ionpac AS 11 4-mm analytical column with functional group of alkanol quaternary ammonium is designed to resolve a number of inorganic anions and organic acid anions from a single sample injection in one gradient run using hydroxide eluent systems such as NaOH used in our experiment.

Samples were prepared as following: A 2 mL sample was diluted 25 times with deionized water with high electrical resistivity (18.2 $\Omega cm$) from Milli-Q Plus ultra-pure water system to avoid overloading the column with inorganic. A disposable syringe with luer-lock tip (Becton Dickinson & Co.) was used to draw about 3 mL of the diluted sample. A Nylon Acrodisc syringe filter (0.2 $\mu m$ pore size, Gelman Science) was used for removal of the biomass present in the sample. During the filtering process, the first 1.5 mL was discarded to allow saturation of the nylon membrane. Subsequently, an amount of filtrate (about 1 mL) was collected using an 1 mL disposable syringe and was injected into the LC 10-2 chromatography organizer for analysis. Although the biomass was removed, the samples were analyzed immediately after preparation in order to exclude the possibility of further nitrate and/or nitrite reduction due to potential presence of active extracellular enzymes.

Activity of microorganisms in the groundwater requires the presence of nutrients. Microorganisms comprise C, H, O, N, P, S, and other trace metals, with a typical molecular formula of cellular composition (on a dry weight basis) as $C_5H_7O_2N_1P_{0.0833}$. For a balanced growth of cells, these elements must be present, in assimilable forms, in the above proportion if a separate electron donor (i.e., carbon source) and an electron acceptor such as oxygen or nitrate is present to meet the energetic need of the microbial cells.

TABLE 3

Summary of groundwater quality data* in the Navajo sandstone in the vicinity of the Tuba City, Arizona, site

| Parameter | Unit | Well 906 | Well 926 | Well 936 |
|---|---|---|---|---|
| Alkalinity as $CaCO_3$ | mg/L | 526–710 | 572–585 | 463–482 |
| Total Dissolved Solids | mg/L | 6800–7600 | 4720–5690 | 10800–13300 |
| Dissolved Oxygen | mg/L | 0.3–8.8 | 2.4–3.1 | 0.6–2.3 |
| Redox Potential | mV | 270–385 | 240–252 | −113–291 |
| PH | s.u | 6.41–6.46 | 6.63–6.64 | 6.52–6.63 |
| Phosphorus as $PO_4^{3-}$ | mg/L | 0.31 | N/A | N/A |
| Calcium | mg/L | 76.1–850 | 67.4–611 | 553–559 |
| Magnesium | mg/L | 354–418 | 329–452 | 168–1450 |
| Molybdenum | mg/L | 0.34–0.46 | 0.01 | 0.01 |
| Selenium | mg/L | 0.035–0.411 | 0.055–0.065 | 0.025–0.136 |
| Strontium | mg/L | 7.43–7.89 | 7.04–7.44 | 8.07–8.58 |
| Nitrate | mg/L | 1300–1410 | 1040–1220 | 3010–3700 |
| Sulfate | mg/L | 2360–2900 | 1830–2050 | 4630–5400 |
| Uranium | mg/L | 0.79–1.14 | 0.248–0.357 | 0.246–0.257 |

*Water quality data based on samples collected between April 95 and April 96

The water quality data of three different wells, which represent the quality of the most contaminated groundwater in situ, are listed in Table 3. As shown in Table 3, nitrate is a main contaminant besides uranium and sulfate which need to be treated, and can serve as an electron acceptor to meet the energetic need of denitrifiers and the remediation purpose. Nitrate can also serve as a nitrogen source for bacterial growth although preferred form of nitrogen source for the cells is ammonium. Hence no nitrogen amendment is needed. The shortage of organic carbon, which serves as both carbon source for bacterial growth and as electron donor for energetic need, should be the main reason for the limited microbial system in situ.

The last essential element for bacterial growth is phosphorus, which has been found in groundwater with limited amount as shown in Table 3. As for phosphate, its chemistry in groundwater and soils is complex. Phosphates are present in dissolved, adsorbed (rapid exchanging), precipitated (medium exchange), and chemisorbed (immobilized) states. All the forms have different rate constants for exchange between the soil and the aqueous phases, and are dependent upon soil pH, clay content and its nature, organics, carbonates, cations, and total phosphates present in the system. Because cell mass contains around 2 to 3% phosphorus, the dissolved phosphate in groundwater, from Well 906 as an example, should be enough to support around 4 mg dry cells/L groundwater. This corresponds to about $10^{10}$ cells/L groundwater, which is a fairly high cell density in an aquifer. In addition, its depletion from groundwater will result in further dissolution of phosphates from soil. Accordingly, there should be no need for additional supply of phosphorus source. However, as shown in Table 4, the addition of phosphorus source is critical for the in situ denitrification of groundwater at Tuba City site.

TABLE 4

Denitrification efficiency of groundwater amended with orthophosphate and other nutrients at 23±1° C.

| Case | Amendment | 0 day | 6 days | 10 days | 15 days | 63 days |
|---|---|---|---|---|---|---|
| 1 | Acetate | 0 | 0 | 0 | N/A | 7–10% |
| 2 | Acetate, core sand | 0 | 0 | 0 | N/A | 9–12% |
| 3 | Acetate, phosphate | 0 | 0 | 0 | N/A | 46–50% |
| 4 | Acetate, phosphate, core sand | 0 | 22–44% | 100% | 100% | 100% |
| 5 | Acetate, phosphate, trace metal | 0 | 18–20% | 30–33% | 100% | 100% |

Figure 1:
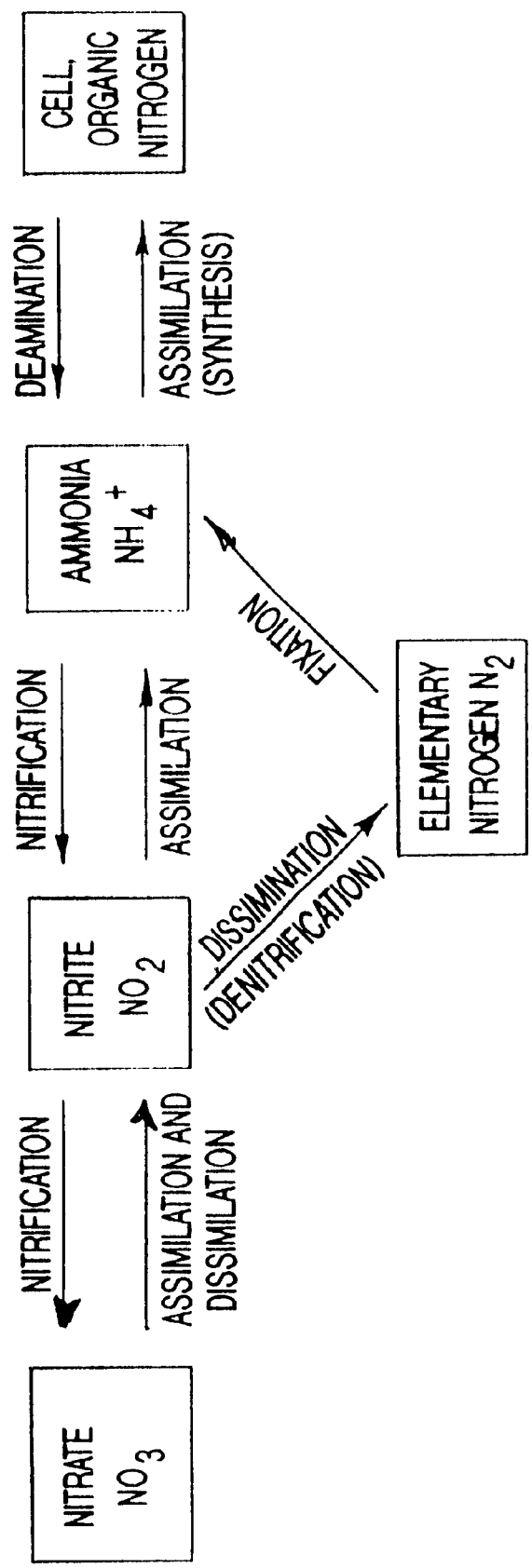
FIG. 1 is a flow chart of the nitrogen cycle main biological processes.
Figure 2:
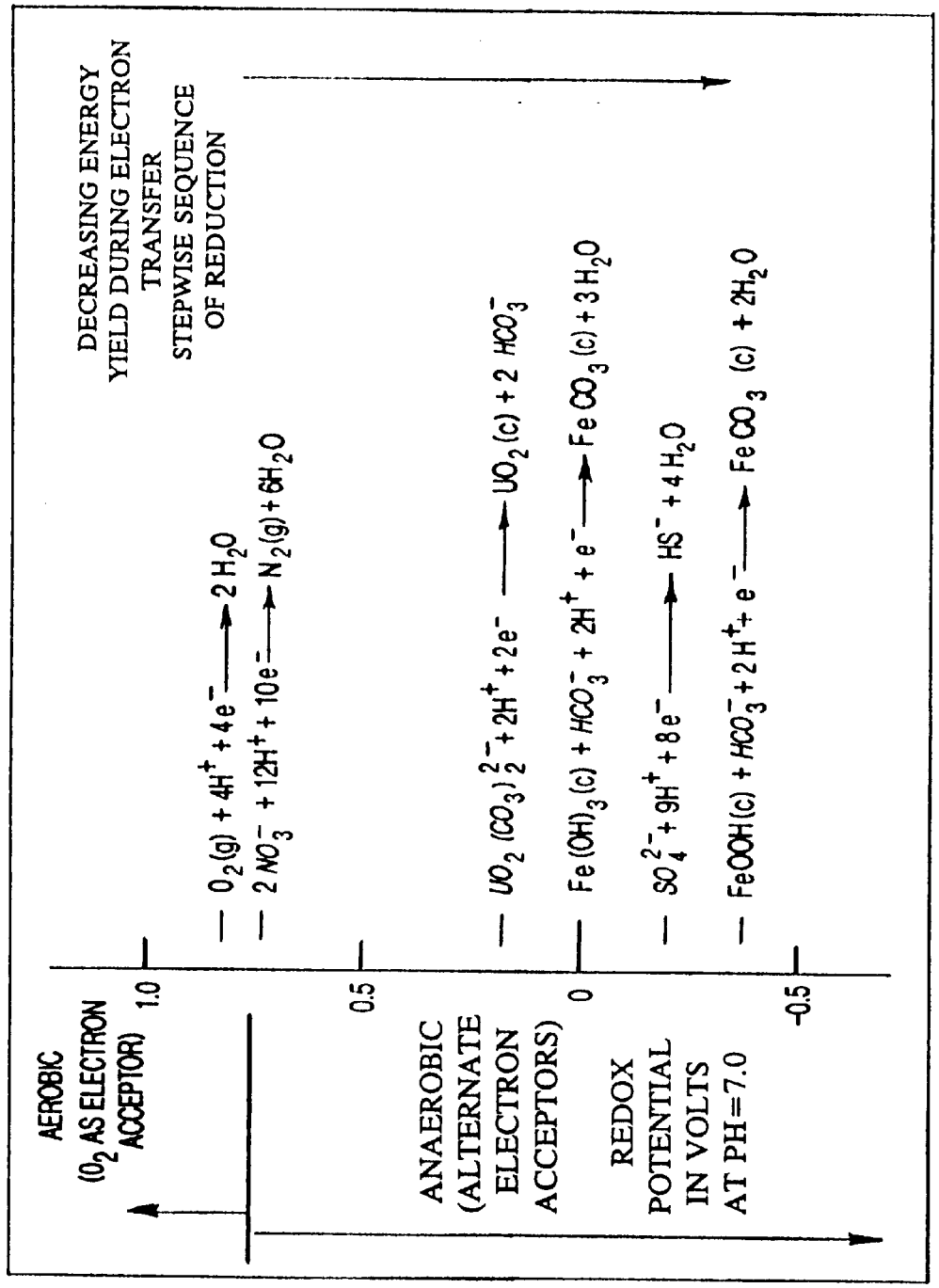
FIG. 2 is a chart of redox potentials of certain electron acceptors significant to in situ denitrification.

Triple serum bottle experiments were run in parallel at room temperature about 23±1° C. The initial concentrations of $NO_3^-$ were in the range of 1200–1400 mg $NO_3^-$/L, and the initial concentration of potassium acetate was in the range of 1200–1300 mg $CH_3COO^-$/L, hence, denitrification was processed under no carbon limitation as will be shown in FIG. 1. $NO_2^-$ was found to be an intermediate during the nitrate reduction process, and it was assumed that one mole of $NO_2^-$ was equivalent to 0.6 mole of $NO_3^-$ based on Equations (2) and (3) when denitrification efficiency was calculated, Precipitate of orthophosphate (0.7–0.8 mM) formed, no mater which form was used ($PO_4^{3-}$, $HPO_4^{2-}$, or $H_2PO_4^-$), because there was a large amount of calcium and magnesium ions in the groundwater.

Very limited nitrate was reduced after 2 months without the amendment of phosphorus source (Case 1 and 2). However, with the addition of orthophosphate, nitrate reduction was amended significantly (Case 3 and 4), and nitrate reduction completed in 10 days with core sand present in the water samples (Case 4). In both Case 3 and 4, dissolved phosphate anions in the bulk solutions were very limited. The nitrate reduction rate in Case 3 was much lower than that in Case 4 in which core sand was present. This can be explained in term of the deficiency of trace minerals (Mn, Fe, Mo etc.) required for bacterial activity in the groundwater, although these trace minerals are present in groundwater (Table 1). The use of trace minerals from groundwater by microorganisms can be compensated by their dissolution from the soil (Case 4) and, hence, their addition are not necessary for in situ remediation. In Case 5, groundwater denitrification was significantly promoted because of the addition of trace metal ion which included 1% v/v of $FeSO_4.7H_2O$ (0.2 g/L) and EDTA (0.5 g/L) mixture, and 0.1% v/v trace nutrient solution ($ZnSO_4.7H_2O$ 0.1 g/L, $MnCl_2.4H_2O$ 0.03 g/L, $H_3BO_3$ 0.3 g/L, $CoCl_2.6H_2O$ 0.2 gL, $CuCl_2.2H_2O$ 0.01 g/L, $NiCl_2.6H_2O$ 0.02 g/L, $NaMoO_4.2H_2O$ 0.03 g/L). Phosphate precipitate was also found because the amount of EDTA added was not enough to complex all calcium and magnesium ions present in the groundwater samples. Phosphate precipitates disappeared after one week, but very limited phosphate species were found in the aqueous phase. Hence, it is reasonable to conclude that the phosphate added had been assimilated by the indigenous denitrifiers. Based on the results in Table 4, following conclusions are summarized: (1) Phosphorous amendment is critical for the in situ biological denitrification, and the dissolution rate of phosphate precipitate does not limit the whole denitrification rate (Case 4 and 5); (2) Trace metal ion amendment is not necessary for the in situ biological denitrification—the amount of trace minerals present in the groundwater is not enough to support bacterial activity, and their use from groundwater by denitrifiers can be compensated by their dissolution from the soil (comparing Case 3 to Case 4 and 5); and (3) Core sand played an important role in the denitrification process, however its function is not clear. It is possible that sand materials supported the denitrifiers, which attached on the surface of the sand particles, a good micro-environment and enough trace metal ions for bacterial growth (comparing Case 4 to 5).

Serum bottle experiments were run at room temperature about 23±1° C. Five different organic carbons, glucose, ethanol, methanol, acetate and lactate, were used for carbon amendment of the groundwater denitrification with core sand present. The initial nitrate concentration in the groundwater samples is in between 1100 and 1550 mg $NO_3^-$/L, and almost no nitrite was present in them (<1 $NO_2^-$ mg/L). Satisfactory denitrification rate was found even if $KH_2PO_4$ concentration was lower than 10 mg/L, however phosphorus limitation was found in this concentration range. A 100 mg/L of $KH_2PO_4$ was supplied for phosphorous amendment, hence denitrification was run under no phosphorus limitation. Resazurin was used as an indicator of redox potential. The solutions showed blue color at the beginning of all experiments because of the presence of resazurin. Then the color changed to purple, pink and finally colorless which meant the redox potential was lower than −100 mV. Denitrification stopped either after the depletion of electron acceptors (i.e., $NO_3^-$ and $NO_2^-$) or after the depletion of electron donors (i.e., amended carbon sources). Depending on the relative amount of carbon added compared to nitrate present, the solutions showed different color after experiments finished. The more the nitrate reduced, the lighter the solution color. Denitrification efficiency ($E_N$) was defined in Equation (11), where i and f refer to initial and final values respectively. The removal efficiency of carbon ($E_C$) was based on the same idea. Only the removal efficiency of acetate and lactate were measured. Initial molar ratios of carbon compound to nitrate for the systems amended with glucose, ethanol and methanol were calculated based on the amount of carbon added and the initial concentration of nitrate measured.

$$E_N = \left(1 - \frac{[NO_3^-]_f}{[NO_3^-]_i}\right) * 100\%, \quad (11)$$

$$E_C = \left(1 - \frac{[Carbon]_f}{[Carbon]_i}\right) * 100\%$$

Nitrite was an intermediate of denitrification process found in all of the experiments. As shown in Equations (12) to (26) and FIGS. 5(a)–(f), nitrogen is mainly supplied as an electron acceptor during the denitrification process. Hence one mole of $NO_2^-$ was assumed to be equivalent to 0.6 mole of $NO_3^-$ when denitrification efficiency was calculated.

Nitrate reduction was studied for a range of initial molar ratio of glucose to nitrate from 2:24 to 20:24 (i.e., C/N from 0.5 to 5). As shown in FIG. 8(a), the minimum molar ratio of glucose to nitrate required for complete denitrification is about 7:24 (i.e., C/N=1.75). When insufficient glucose is added (i.e., the initial molar ratio is less than 7:24), complete denitrification is not reached, however, denitrification efficiency increases linearly with an increase of C/N ratio. The dashed line and the solid line represent the theoretical denitrification efficiency and the glucose removal efficiency respectively based on the assumption that the overall molar ratio of glucose to nitrate is 7:24 for the combination of bacterial synthesis and energy supply. The same idea were used for the systems amended with ethanol, methanol, acetate and lactate. It is shown that the experimental data fit the theoretical curves very well. Acetate was found to be an intermediate during glucose metabolism. Based on the assumption that glucose and nitrate either react to supply energy or provide carbon and nitrogen elements for creating new cell mass in heterotrophic denitrifiers, the following approximate stoichiometric equations which represent both bacterial synthesis and energetic supply can be obtained. According to Equation (7), the theoretical yield coefficients are approximately equal to 0.187 g dry cell/g glucose (i.e., 0.468 g dry cell/g C) and 0.158 g dry cell/g $NO_3^-$ based on glucose and nitrate respectively.

Energy: $5C_6H_{12}O_6 + 24NO_3^- + 6OH^- \rightarrow 12N_2\uparrow + 30HCO_3^- + 18H_2O$ (12)

Synthesis: $7C_6H_{12}O_6 + 6NO_3^- + 6OH^- \rightarrow 6C_5H_7O_2N + 18H_2O + 12HCO_3^-$ (13)

Overall stoichiometry: $7C_6H_{12}O_6 + 24NO_3^- + 7.565OH^- \rightarrow 10.957N_2\uparrow + 2.087C_5H_7O_2N + 31.565HCO_3^- + 22.696H_2O$ (14)

Figure 5A:
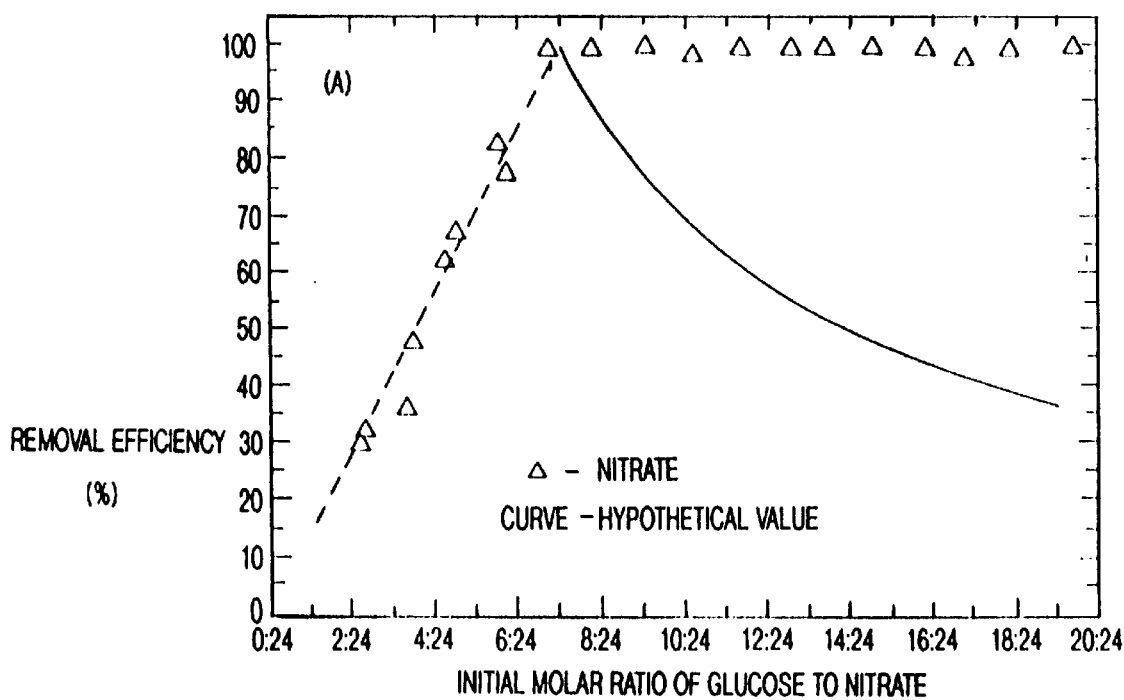
FIGS. 5(a)–(f) illustrate effects of initial molar ratio of carbon compound to nitrate on denitrification efficiency of groundwater with core sand present amended with glucose, ethanol, methanol, acetate, or lactate as carbon sources and $KH_2PO_4$ as a phosphorus source, and the denitrification time requirement (dashed line represents hypothetical value of denitrification efficiency; solid line represents hypothetical value of carbon removal efficiency)
Figure 5B:
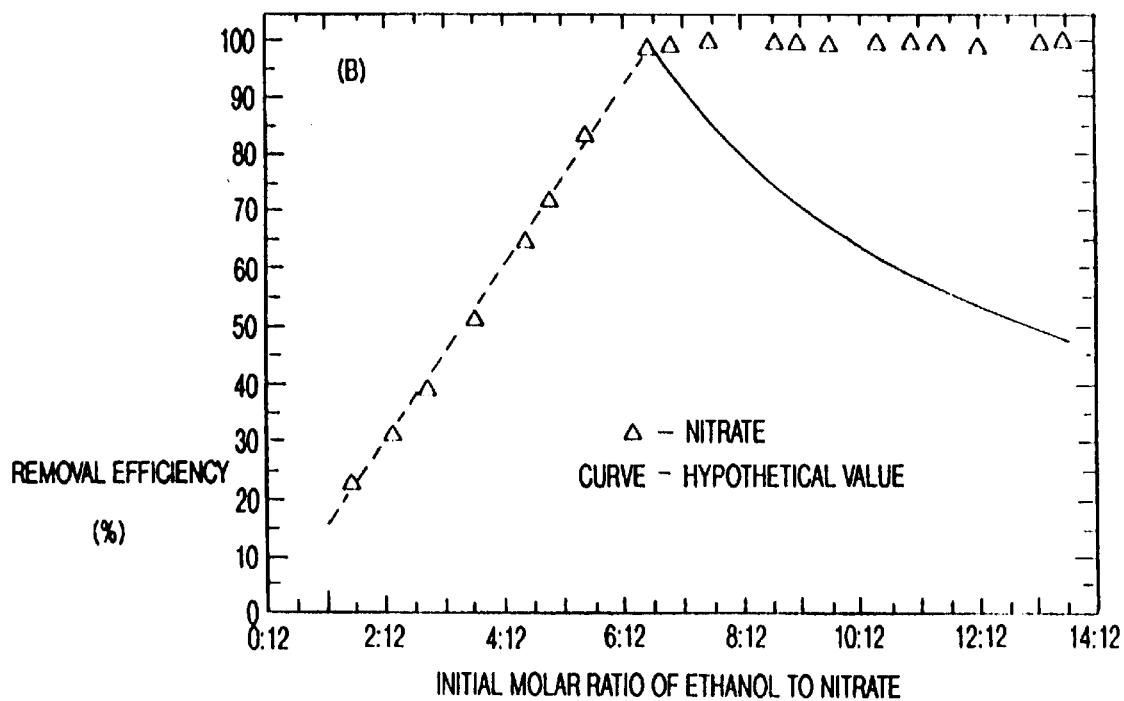

The experimental result of denitrification with ethanol as a carbon source is shown in FIG. 5(b) with initial molar ratio of ethanol to nitrate from 1.2:12 to 13.5:12 (i.e., C/N from 0.2 to 2.25). The minimum molar ratio of ethanol to nitrate required for complete denitrification is about 6.5:12 (i.e., C/N=1.083). When insufficient ethanol is added (i.e., the initial molar ratio is less than 6.5:12), complete denitrification is not reached, however, denitrification efficiency increases linearly with an increase of C/N ratio. Acetate was also found to be an intermediate during ethanol metabolism. Denitrification efficiency is still high even when initial molar ratio of ethanol to nitrate increases to 14:12. This means that the activity of denitrifiers was not inhibited when ethanol concentration used was as high as 25 mM (initial concentration of nitrate was about 21 mM). As shown in FIG. 5(b), the experimental data fit the theoretical curves very well which were obtained using the same method as that used for glucose. Similar stoichiometric equations can also be obtained for heterotrophic denitrifiers using ethanol as both electron donor and carbon element for new cell mass. According to Equation (10), the theoretical yield coefficients are approximately equal to 0.295 g dry cell/g ethanol (i.e., 0.565 g dry cell/g C) and 0.118 g dry cell/g $NO_3^-$ based on ethanol and nitrate respectively.

Energy: $5C_2H_5OH + 12NO_3^- + 2H^+ \rightarrow 6N_2\uparrow + 10HCO_3^- + 11H_2O$ (15)

Synthesis: $7C_2H_5OH + 3NO_3^- + HCO_3^- + 4H^+ \rightarrow 3C_5H_7O_2N + 13H_2O$ (16)

Overall stoichiometry: $6.5C_2H_5OH + 12NO_3^- + 2.913H^+ \rightarrow 5.609N_2\uparrow + 0.783C_5H_7O_2N + 9.087HCO_3^- + 13.674H_2O$ (17)

Figure 5C:
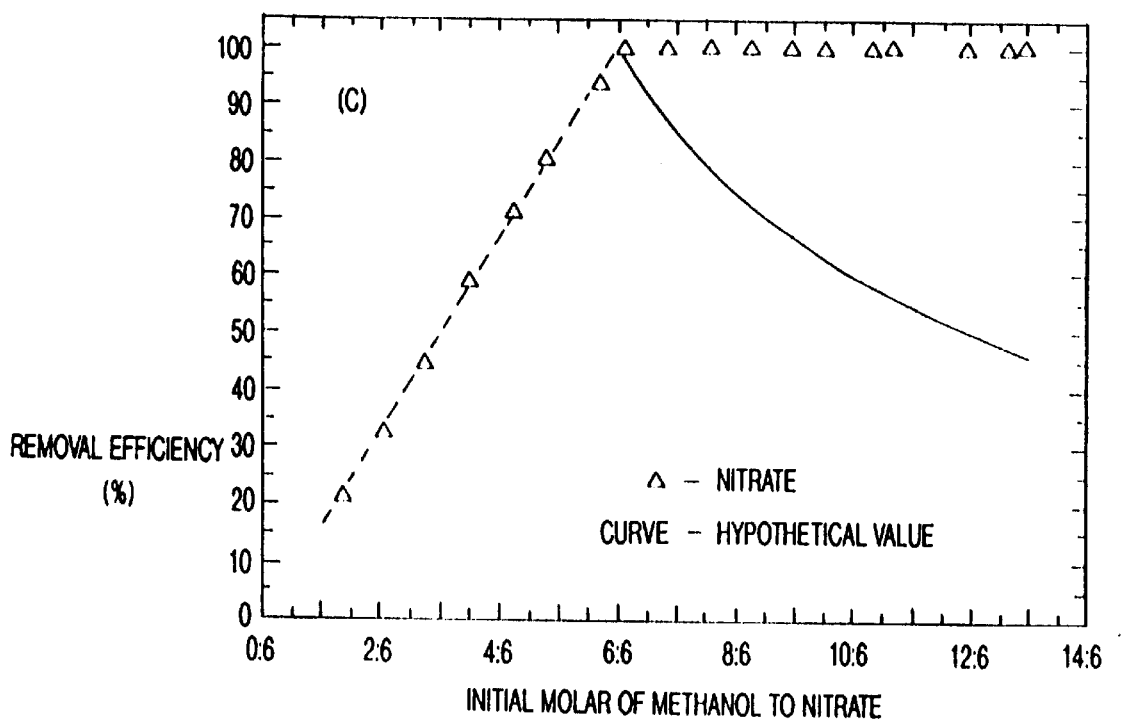

The experimental result of denitrification with methanol as a carbon source was similar to that of glucose and ethanol. Initial molar ratios of methanol to nitrate were controlled in between 1.2:6 to 13:6 (i.e., C/N from 0.2 to 2.2). As shown in FIG. 5(c), the minimum molar ratio of methanol to nitrate required for complete denitrification is about 6:6 (i.e., C/N= 1). Denitrification efficiency increases linearly with an increase of C/N ratio when insufficient methanol is added (i.e., the initial molar ratio is less than 6:6). With further increase of the initial molar ratio of methanol to nitrate until 13:6, denitrification efficiency still maintains at 100%. This means that the activity of denitrifiers was not inhibited when methanol concentration used was as high as 45 mM (initial concentration of nitrate was about 21 mM). As shown in FIG. 5(c), the experimental data fit the theoretical curves very well which was obtained using the same method as that used for glucose and ethanol. Similar stoichiometric equations can also be obtained for heterotrophic denitrifiers using methanol as both electron donor and carbon element for new cell mass. According to Equation (20), the theoretical yield coefficients are approximately equal to 0.153 g dry cell/g methanol (i.e., 0.408 g dry cell/g C) and 0.079 g dry cell/g $NO_3^-$ based on methanol and nitrate respectively.

Energy: $5CH_3OH+6NO_3^-+H^+ \rightarrow 3N_2\uparrow+5HCO_3^-+8H_2O$ (18)

Synthesis: $14CH_3OH+3NO_3^-+HCO_3^-+4H^+ \rightarrow 3C_5H_7O_2N+20H_2O$ (19)

Overall stoichiometry: $6CH_3OH+6NO_3^-+1.304H^+ \rightarrow 2.870N_2\uparrow+0.261C_5H_7O_2N+4.696HCO_3^-+9.391H_2O$ (20)

Figure 5D:
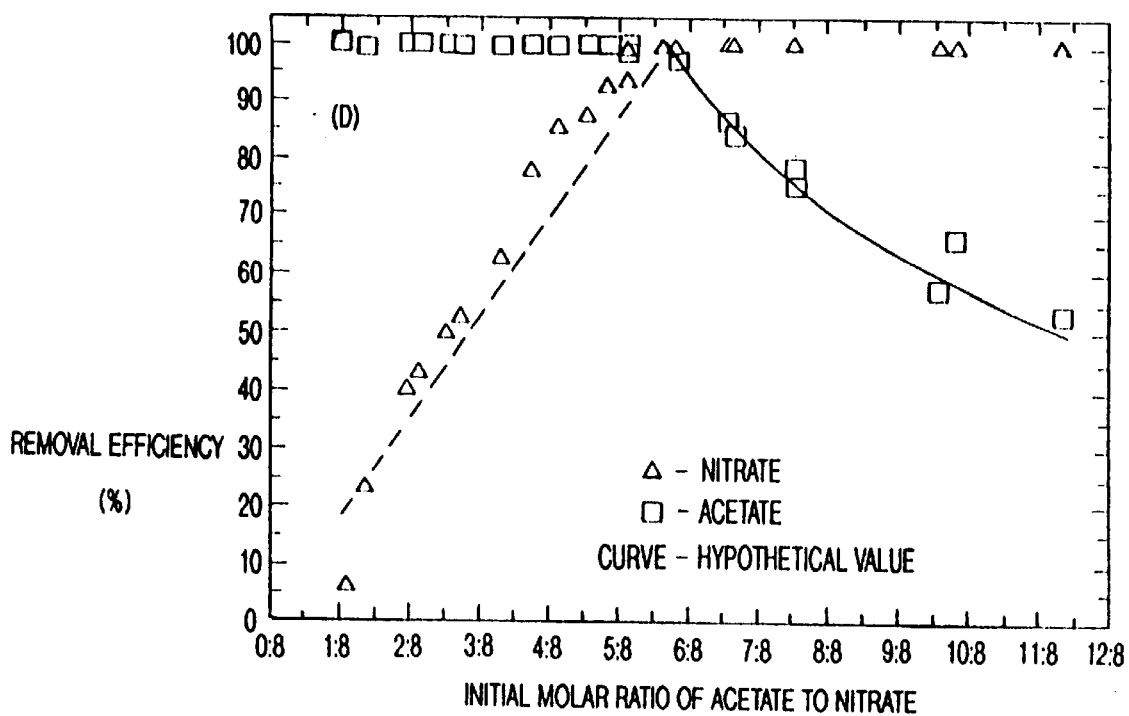

The experimental result of denitrification with acetate as a carbon source is shown in FIG. 5(d) with initial molar ratios of acetate to nitrate controlled in between 1:8 to 11.5:8 (i.e., C/N from 0.25 to 2.9). The minimum molar ratio of acetate to nitrate required for complete denitrification is about 5.7:8 (i.e., C/N=1.425). Denitrification efficiency increases near linearly with an increase of C/N ratio when insufficient acetate is added. As shown in FIG. 5(d), the experimental data fit the theoretical curves quite well for both nitrate reduction efficiency and acetate removal efficiency. Similar stoichiometric equations can also be obtained for heterotrophic denitrifiers using acetate as both electron donor and carbon element for new cell mass. According to Equation (23), the theoretical yield coefficients are approximately equal to 0.081 g dry cell/g acetate (i.e., 0.198 g dry cell/g C) and 0.055 g dry cell/g $NO_3^-$ based on acetate and nitrate respectively.

Energy: $5CH_3COO^-+8NO_3^-+3H^+ \rightarrow 4N_2\uparrow+10HCO_3^-+4H_2O$ (21)

Synthesis: $7CH_3COO^-+2NO_3^-+5H^+ \rightarrow 2C_5H_7O_2N+4HCO_3^-+4H_2O$ (22)

Overall stoichiometry: $5.7CH_3COO^-+8NO_3^-+3.517H^+ \rightarrow 3.878N_2\uparrow+0.243C_5H_7O_2N+10.183HCO_3^-+4.365H_2O$ (23)

Figure 5E:
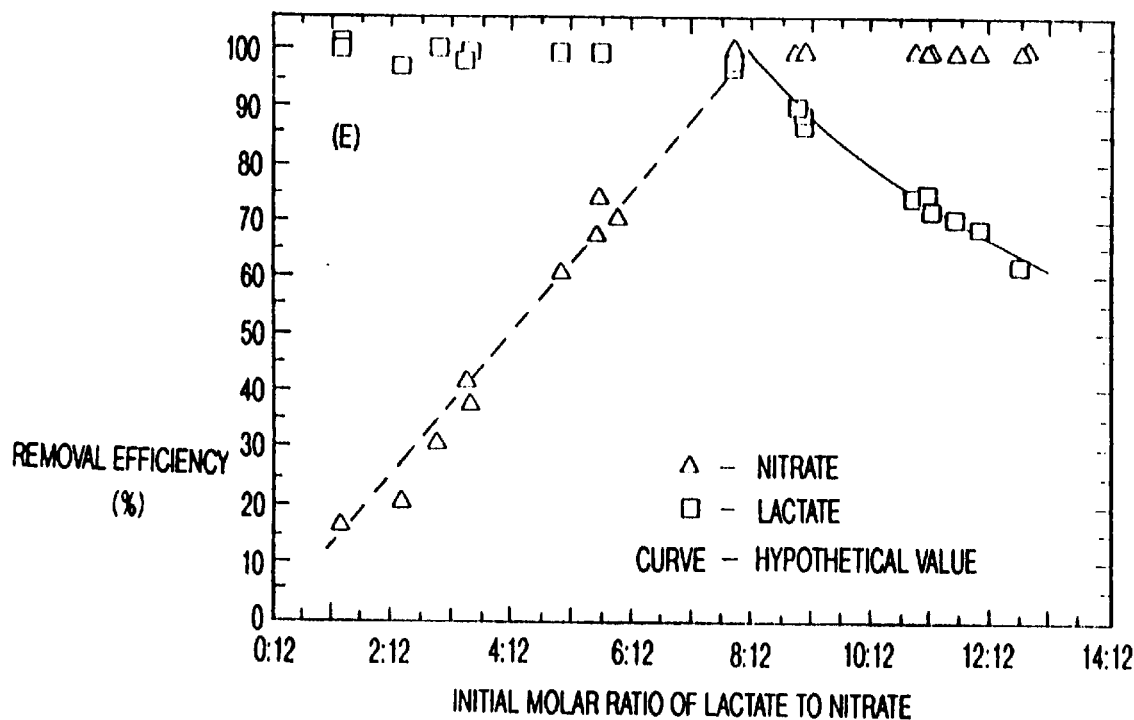

Lactate was also used as a carbon source for denitrification amendment with initial molar ratios of lactate to nitrate controlled in between 1:12 to 12.8:12 (i.e., C/N from 0.25 to 3.2). As shown in FIG. 5(e), the minimum molar ratio of lactate to nitrate required for complete denitrification is about 8:12 (i.e., C/N=2). Denitrification efficiency increases linearly with an increase of C/N ratio when insufficient lactate is added. It was found that acetate was an intermediate during lactate metabolism. Based on the theoretical equations for energy supply using acetate and lactate as electron donors as shown in equation (21) and (24), 1 mole of acetate was assumed to be equivalent to 2/3 mole of lactate for denitrification when lactate removal efficiency was calculated. As shown in FIG. 5(e), the experimental data fit the theoretical curves quite well for both nitrate reduction efficiency and lactate removal efficiency. Stoichiometric equations can also be obtained for heterotrophic denitrifiers using lactate as both electron donor and carbon element for new cell mass. According to Equation (26), the theoretical yield coefficients are approximately equal to 0.248 g dry cell/g lactate (i.e., 0.614 g dry cell/g C) and 0.238 g dry cell/g $NO_3^-$ based on lactate and nitrate respectively.

Energy: $5CH_3CH(OH)COO^-+12NO_3^-+2H^+ \rightarrow 6N_2\uparrow+15HCO_3^-+6H_2O$ (24)

Synthesis: $7CH_3CH(OH)COO^-+3NO_3^-+4H^+ \rightarrow 3C_5H_7O_2N+6H_2O+6HCO_3^-$ (25)

Overall stoichiometry: $8CH_3CH(OH)COO^-+12NO_3^-+3.826H^+ \rightarrow 5.217N_2\uparrow+1.565C_5H_7O_2N+8.348H_2O+16.174HCO_3^-$ (26)

Figure 5F:
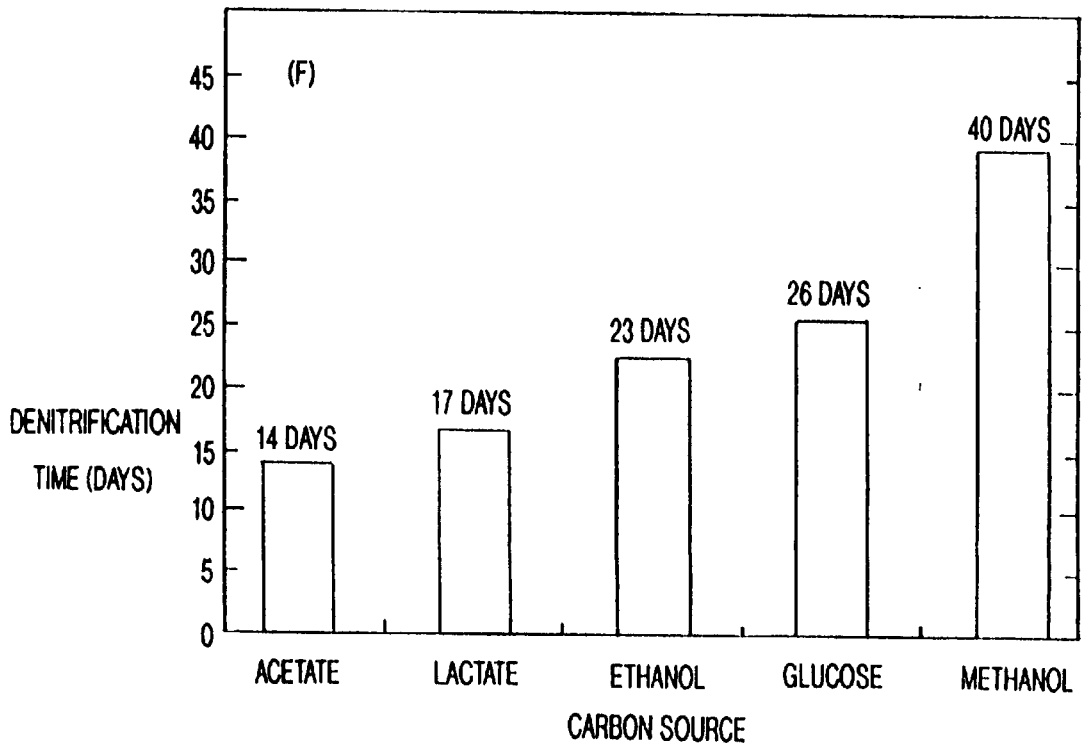

The time requirement shown in FIG. 5(f) is the denitrification time of groundwater amended with orthophosphate and different carbon sources via the activity of denitrifiers present in the water samples. Denitrification time was related to many parameters such as pH, initial bacterial concentration, and experimental conditions. The times listed in FIG. 5(f) are the times for the whole group of the experiments to be finished. It is shown that acetate is a most readily available carbon source for denitrification, lactate follows acetate, ethanol and glucose takes about 3.5 weeks, and methanol is the most difficult carbon source to be metabolized although methanol is most commonly used external carbon source based on cost and availability on the market. The advantage of using methanol is that the methanol residual can be removed by aeration. A long adaptation time and slower denitrification rate seems to be two major disadvantages of methanol as a carbon source for satisfactory denitrification. As shown in FIG. 5(f), ethanol is a more readily available carbon source for denitrification than is methanol, and could be another possible carbon source used for water denitrification, but it is more expensive than methanol in pure form. Pseudomonas and Acinetobacter are predominating bacteria species in the reactor with ethanol as electron donor. Denitrification with ethanol is much more stable throughout the chemostat experiment than is the denitrification with methanol, and the maximum growth rate of denitrifiers to be 2–3 times higher with ethanol than with methanol. However, Hyphomicrobium was found not to dominate in the denitrifying methanol enrichment. Glucose is an expensive chemical and was not used as fast as ethanol. Although lactate is a more readily available carbon compound for denitrification, its cost should be a major factor need to be considered in commercial use.

TABLE 5

Appropriate values of C/N ratios for nearly complete denitrification and theoretical yield coefficient, Y, with base of nitrate

| Carbon source | C/N molar ratio | Y (g DW cell/g $NO_3^-$) |
|---|---|---|
| Methanol | 1.000 | 0.079 |
| Ethanol | 1.083 | 0.118 |
| Acetate | 1.425 | 0.055 |
| Glucose | 1.750 | 0.158 |
| Lactate | 2.000 | 0.238 |

Appropriate values of the C/N molar ratios for complete denitrification amended with five different carbon sources are summarized in Table 5. The actual C/N molar ratio for complete denitrification increases with the complexity of carbon source. The theoretical yield coefficients based on nitrate removal with methanol and acetate as carbon sources are lower that those with other three carbon materials. Low bacterial yield is often critical for in situ bioremediation because bacterial fouling is frequently met.

Figure 6:
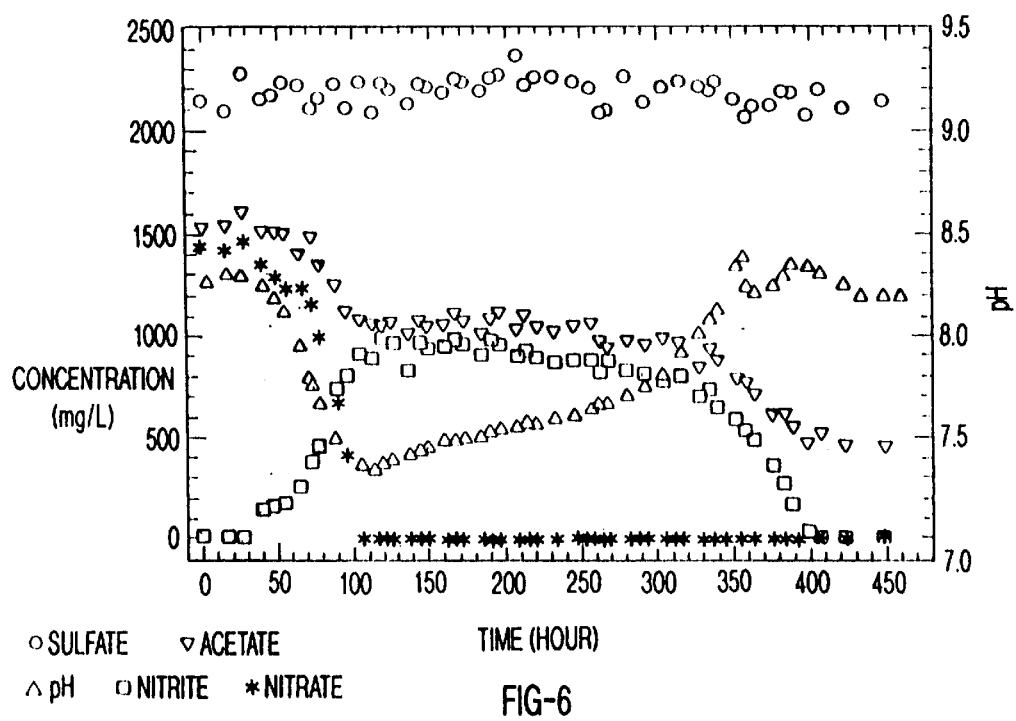
FIG. 6 is a graph of concentration profiles in a batch reactor operated at 16° C.

Denitrification of groundwater amended with acetate and $KH_2PO_4$ was monitored in a 2.5 L bioreactor. Temperature was controlled at 16° C. which is the typical groundwater temperature at site. The concentration change of acetate, nitrate, nitrite, and the pH change are shown in FIG. 6. Sulfate concentration is also shown.

Obviously, there are five different phases in FIG. 6. There is a lag phase until about 30 hours. In this phase, no concentration change of acetate and nitrate, and no nitrite formation are found. In the period between about 30 and 110 hours, nitrate is reduced to nitrite. Nitrate ion concentration goes down to zero and nitrite ion concentration reaches to its maximum value in 110 hours. The concentration profiles of nitrate and nitrite are almost near symmetrical in this phase, if the concentration profiles are plotted in the unit of molar concentration, although more nitrate is reduced compared to the formation of nitrite. Hence, denitratation, reduction of $NO_3^-$ to $NO_2^-$, dominates in this period, and denitritation, reduction of $NO_2^-$ to NO or directly to $N_2$, with low activity is also present. There is another lag phase in between 110 and 200 hours. Almost no concentration changes of acetate and nitrite are found in this period. Denitritation is almost inhibited completely by high nitrite concentration. Obvious denitritation is found after 200 hours. The lower the concentration of nitrite, the quicker the denitritation rate. The denitritation completes in 400 hours. Concentrations of nitric oxide and nitrous oxide in the gas phase were not monitored in the experiment. It is found in FIG. 6 that the concentration of acetate levels off after 400 hours, which means the completion of denitrification. Hence, it is reasonable to suggest that the reduction rates of both nitric and nitrous oxides are much quicker than denitratation and denitritation rate, if nitric and nitrous oxides are the two denitrification intermediates. Sulfate reduction was not found in the experimental period.

With regard to pH, its profile was related to several different factors such as denitrification, both denitratation and denitritation, carbonate buffer effect, and the presence of sand with carbonate deposits, mainly $CaCO_3$ and some $MgCO_3$, on its surface. As shown in FIG. 6, pH increases during the first 16 hours, and then kept constant until 30 hours. This is probably because equilibrium of Equation (19) and (20) are unbalanced after purging with argon gas to the water in the reactor at the beginning of the experiment. Carbon dioxide is much more soluble than oxygen, and is not easy to be totally taken off by purging with argon gas for about 15 min. Both reactions process in the direction to the left sides until equilibria reach, and result in the increase of pH.

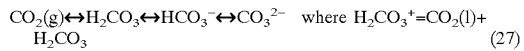

$$CO_2(g) \leftrightarrow H_2CO_3 \leftrightarrow HCO_3^- \leftrightarrow CO_3^{2-} \text{ where } H_2CO_3^* = CO_2(l) + H_2CO_3 \quad (27)$$

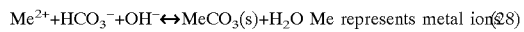

$$Me^{2+} + HCO_3^- + OH^- \leftrightarrow MeCO_3(s) + H_2O \text{ Me represents metal ion} \quad (28)$$

In the second phase between about 30 and 110 hours, denitratation, as described in Equation (29), leads to the decrease of pH until the concentration of nitrate reaches to zero.

$$4NO_3^- + CH_3COO^- \rightarrow 4NO_2^- + 2HCO_3^- + H^+ \quad (29)$$

In the fourth phase where significant denitritation is found, pH increases significantly. The quicker the denitritation rate, the quicker the pH increase, which could be explained using Equation (30).

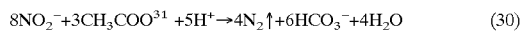

$$8NO_2^- + 3CH_3COO^{3-} + 5H^+ \rightarrow 4N_2\uparrow + 6HCO_3^- + 4H_2O \quad (30)$$

In the third phase, i.e., another lag phase in between about 110 and 200 hours, pH increase is also found. This is probably because of the dissolution of carbonate deposits as shown in Equation (28), mainly $CaCO_3$ and some $MgCO_3$, from the sand surface due to the relative low pH after denitratation. Two pH fluctuations are found after about 355 hours. The decreases of pH in this period could be explained as the result of the precipitation of carbonate salts due to the relative high pH increase in the denitritation phase. Lots white precipitate, i.e., carbonate particles, was found on the reactor surface and sand surface during the end of the experiment. Solution pH continues to decrease after denitritation completes and levels at pH 8.19. This leveled pH is almost the same as the equilibrium pH, which is 8.30, before denitratation began in the first lag phase. This phenomenon can be explained using the buffering effect of carbonate in aqueous and carbonate precipitate on the sand surface as shown in Equations (27) and (28). A little bit decrease of pH from 8.3 to 8.19 could be explained by the formation of carbon dioxide due to the oxidation of acetate. The total processes including buffering effect of carbonate and denitrification raise the pH from 7.92 to 8.19. It is worth mentioning that the dominant species of carbonates is $HCO_3^-$ in the pH range between 6.41 and 10.37, which is critical for Equations (29) and (30).

Figure 7:
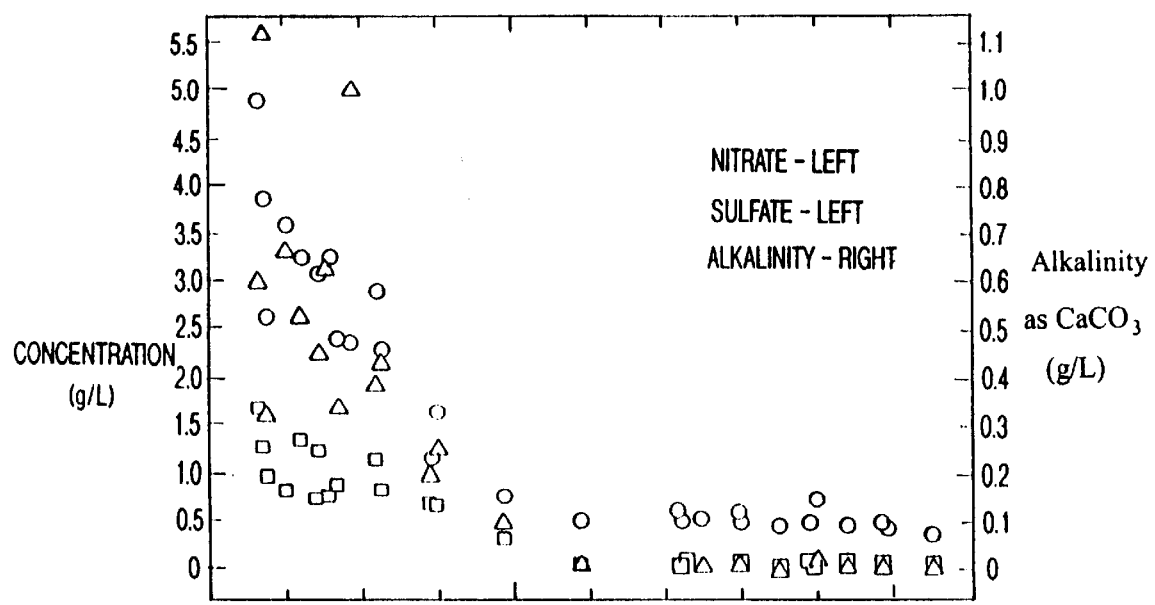
FIG. 7 is a graph of contaminant concentrations in monitoring wells with their groundwater pH.

Microorganisms can use only orthophosphate for biochemical processes. Therefore, the bioavailability of phosphorus in the course of a bioremediation process depends on the presence of orthophosphate. Nearly all in situ bioremediation projects use orthophosphates as an added phosphorus source, however, the addition of orthophosphates often leads to precipitation of insoluble phosphates, which plug infiltration wells and surrounding aquifers, and hence short migration of phosphorus source. For the contaminated groundwater at Tuba City cite, the groundwater pH is quite wide, from acidic to basic, which depends on the extent of contamination as shown in FIG. 7. The higher the contaminant concentration, the lower the pH. The groundwater with pH range from 6.3 to 7.2 represents the most contaminated zones. Hydrogen phosphate and dihydrogen phosphate dominate in this pH range theoretically. With regard to orthophosphate precipitates, hydrogen phosphate is much more insoluble than dihydrogen phosphate. Hence, it is difficult to control the phosphate precipitation during in situ denitrification. In addition to phosphate precipitation, sorption of orthophosphate to soil is very strong. No mobilization or solubilization of these retarded orthophosphates is observed in normal groundwater with a pH of 6 to 9.

Concerning the precipitation of orthophosphate, the bioavailability of different inorganic phosphates was studied. One candidate is polyphosphate, $(NaPO_3)_n$, with different chain length from diphosphate $(Na_4P_2O_7)$, tripolyphosphate $(Na_5P_3O_{10})$, to even $Na_{20}P_{18}O_{55}$. With increasing chain length (>5 P-atoms) of polyphosphates, the intensity of their interaction with soil decreases. The shorter polyphosphates such as diphosphate, tripolyphosphate also exhibit interaction with the soil matrices, but their retardation is more reversible than the retardation of orthophosphate. However, polyphosphates degrade rapidly in soil and form ortho-compounds. The hydrolysis of polyphosphates can be described as a function of pH, biological activity, and temperature. The denitrification profiles of groundwater amended with polyphosphate, $(NaPO_3)_n$, and different carbon sources with the presence of core sand are shown in FIGS. 8(a) and (b). Experiments were run in serum bottles at room temperature about 23±1° C. The concentration of polyphosphate was 100 mg $NaPO_3$/L. The initial molar ratios of acetate to nitrate and glucose to nitrate were about 10:8 and 11:24 respectively, and hence no carbon limitation was present in these two experiments as discussed in FIGS. 5(a)–(f). The initial molar ratios of ethanol to nitrate and methanol to nitrate were about 5:12 and 5.5:6 respectively, and hence complete nitrate reduction could not reach for these two experiments. Nitrite was an intermediate of denitrification process found in all of the experiments, and one mole of $NO_2^-$ was assumed to be equivalent to 0.6 mole of $NO_3^-$ when nitrate removal efficiency was calculated.

As shown in FIGS. 8(a) and (b), nitrate reduction with acetate as a carbon source completes in 15 to 25 days. For ethanol, nitrate reduction stops after about 30 days (denitrification has not completed). For these two carbons, the denitrification time with polyphosphate is about 5 to 10 days longer than that with orthophosphate. The difference of the denitrification rates could be due to the hydrolysis of polyphosphate, because microorganisms can use only orthophosphate for biochemical processes. However, for glucose and methanol, denitrification rate with polyphosphate is much slower than that with orthophosphate, because the hydrolysis of polyphosphate is mainly due to biological activity besides chemical effect at lower temperature. It is help to mention that the biological activities with different carbon amendments are in the decreasing order from acetate, ethanol, glucose to methanol as shown in FIG. 5(f). Hence, it is reasonable to conclude that the hydrolysis of the polyphosphate is the rate-limiting step when using it as a phosphorus source for in situ denitrification.

For all the experiments amended with polyphosphate, precipitate was found right after purging with argon because the chemical hydrolysis of polyphosphate was accelerated by this purging process, i.e., de-oxygen and de-carbon dioxide which will lead to increase of pH. Only 5% nitrate was reduced after 2 months when acetate was amended as a carbon source if core sand was not present. Very limited nitrate reduction rate (0–2% of nitrate was reduced after 2 months) was found for ethanol, methanol and glucose. This phenomenon verified the function of sand again in in situ bioremediation. The nitrate reduction profiles for the experiment amended with acetate and polyphosphate but without addition of sand material and without purging argon is also shown in FIGS. 8(a) and (b). Nitrate reduction completes in 40 to 47 days. The denitrification rate is lower than that with sand material present. It is partly due to the presence of oxygen in the serum bottle (the water sample was oxygenated during transferring water from 1 L plastic bottle to serum bottles, and about 60 mL air gas present in the serum bottle) and the deficiency of trace metal ions in water. Phosphate precipitate was not found because without purging with argon. The presence of phosphorus and trace minerals in the liquid phase is the possible reason for the relative fast denitrification rate compared to the Case 3 shown in Table 4 in which both phosphate and trace minerals precipitated.

Besides polyphosphate, trimetaphosphate (TMP), $Na_3P_3O_9$, is another candidate for phosphorus source instead of orthophosphates. TMP is a ring compound, and hence is more stable than polyphosphates. TMP has a slow rate of hydrolysis and its sorption in soils is also low. The denitrification profiles of groundwater amended with TMP and acetate with or without the presence of core sand are shown in FIGS. 9(a) and (b). No phosphate precipitation was found after purging with argon. Experiments were run in serum bottles at 16° C. The concentration of TMP was 100 mg $NaPO_3/L$. No phosphate precipitate was found in three weeks. This time is enough for phosphate transportation into the whole contaminated aquifer, and no plugging problem of the infiltration wells due to the precipitation of insoluble phosphate salts will happen if the wells are designed properly. As shown in FIGS. 9(a) and (b), denitrification completes in 28 days with the presence of sand. This time is 11 days longer than that amended with orthophosphate as shown in FIG. 6. The hydrolysis rate of TMP limits the whole remediation rate, although the nitrate reduction rate is also slow at 16° C. However, this time difference will not be a critical issue for the in situ operation. Compared to the quick denitratation rate as shown in FIG. 6, denitratation and denitritation rate are comparable for the systems amended with TMP as shown in FIGS. 9(a) and (b). For the systems without the presence of sand, the denitrification rate is very slow. This phenomenon confirmed the positive effect of sand materials on the in situ denitrification again.

Accordingly, the following conclusions were reached from the experiments of this Example:

(1) In situ biological denitrification is a successful method to remediate nitrate contaminated groundwater at a DOE Uranium Mill Tailings Site. Nitrate can be rapidly reduced to below EPA standards by the indigenous denitrifiers if suitable carbon and phosphorus sources were amended. No addition of trace minerals is needed. This technology is a potential effective method for nitrate removal from groundwater.

(2) In the batch systems, nitrate was reduced completely while the C/N ratio was properly controlled. The minimum C/N ratio for complete denitrification were 1.000, 1.083, 1.425, 1.750, 2.000 for the systems with methanol, ethanol, acetate, glucose and lactate as carbon sources respectively. Nitrite was found to be a nitrate reduction intermediate in all of the experiments, and acetate was found to be an intermediate during the metabolism of ethanol, lactate and glucose. Stoichiometric equations were obtained for heterotrophic denitrifiers using amended carbon sources as both electron donor and carbon element for new cell mass. Theoretical yield coefficients were estimated based on the stoichiometric equations.

(3) For the system amended with acetate, pH change during denitrification process was found to be related to denitratation rate, denitritation rate and carbonate buffering effect. Denitratation led to decrease of pH and denitritation led to increase of pH. Nitrite inhibition in high concentration to denitrification was found.

(4) Concerning the precipitation of orthophosphate and hence the plugging of the infiltration well and short migration of phosphate, polyphosphate and trimetaphosphate, especially trimetaphosphate, were found to be two desirable form of phosphate for injection.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of anaerobic in situ biodenitrification of a contaminated site, the method comprising the steps of:

providing to a site contaminated with nitrate a phosphorus source selected from the group consisting of polyphosphates and trimetaphosphates; and permitting indigenous microbes to anaerobically convert substantially all nitrate and nitrite to nitrogen gas.

2. The method of claim 1 wherein the providing step comprises providing a phosphorus source to a saturated zone.

3. The method of claim 1 wherein the providing step comprises providing a phosphorus source to an unsaturated zone.

4. The method of claim 1 additionally comprising the step of providing to the site a carbon source.

5. The method of claim 4 wherein the step of providing a carbon source comprises providing acetate.

6. An anaerobic in situ biodentrification apparatus comprising at least one extraction well for extracting subsurface water from a contaminated site, a container for mixing nutrients into the extracted water, and an injection well for re-introducing the extracted water to the subsurface; wherein the nutrients comprise a phosphorus source selected from the group consisting of polyphosphates and trimetaphosphates; and wherein the nutrients exclude a nitrogen source.

7. The apparatus of claim 6 comprising at least three extraction wells placed approximately on a circle having said injection well as a center.

8. A method of anaerobic biodentrification of a contaminated site, the method comprising the steps of:
   a) sampling groundwater of the contaminated site;
   b) determining levels of nitrate contamination from the sampled groundwater;
   c) choosing preferred nutrients to be injected into the contaminated site, wherein the nutrients comprise a phosphorus source selected from the group consisting of polyphosphates and trimetaphosphate;
   d) configuring size, geometry, and pumping rates for wells to be installed at the site; and
   e) installing and operating one or more well clusters at the site until the subsurface is denitrified to a desired level by permitting indigenous microbes to anaerobically convert substantially all nitrate and nitrite to nitrogen gas.

9. The method of claim 8 additionally comprising at least one step from the group consisting of determining levels of nutrients, determining levels of dissolved oxygen, determining levels of phosphates, generating reaction curves for predetermined constituents at the site, verifying shape of the reaction curves to determine whether significant chemical reactions other than denitrification are occurring, gathering contaminate concentration and hydrological data at the site, and installing and testing a single well cluster at the site.

* * * * *